United States Patent [19]
Cozzi et al.

[11] Patent Number: 6,165,980
[45] Date of Patent: Dec. 26, 2000

[54] DISTAMYCIN DERIVATIVES, PROCESS FOR PREPARING THEM, AND THEIR USE AS ANTITUMOR AND ANTIVIRAL AGENTS

[75] Inventors: Paolo Cozzi, Milan; Italo Beria, Villamarzana; Marina Caldarelli; Maria Cristina Geroni, both of Milan; Enrico Pesenti, Cologno Monzese, all of Italy

[73] Assignee: Pharmacia & Upjohn S.p.A., Milan, Italy

[21] Appl. No.: 09/101,758

[22] PCT Filed: Jan. 22, 1997

[86] PCT No.: PCT/EP97/00369

§ 371 Date: Jul. 17, 1998

§ 102(e) Date: Jul. 17, 1998

[87] PCT Pub. No.: WO97/28123

PCT Pub. Date: Aug. 7, 1997

[30] Foreign Application Priority Data

Feb. 2, 1996 [GB] United Kingdom ............... 9602163
Jul. 3, 1996 [GB] United Kingdom ............... 9613987

[51] Int. Cl.$^7$ ............................................. A61K 38/00
[52] U.S. Cl. .................... 514/19; 514/18; 514/422; 514/256; 514/396; 514/397; 548/518; 548/314.7; 544/333
[58] Field of Search ............... 514/422, 19, 256, 514/396, 397, 18; 548/518, 314.7; 544/333; 530/331

[56] References Cited

FOREIGN PATENT DOCUMENTS 0 246 868  11/1987  European Pat. Off. .

OTHER PUBLICATIONS

D'Alessio et al., "Structure–Activity Relationship of Novel Distamycin a Derivatives: Synthesis and Antitumor Activity" Bioorg. Med. Chem. Lett., vol. 4, No. 12, 1994, 1467–1472.

Wyatt et al., "Structure–activity Relationship of a Series of Nitrogen Mustard– and Pyrrole–Containing Minor Groove–Binding Agents Related to Distamycin" Anti–Cancer Drug Design 9:511–525, 1994.

*Primary Examiner*—E. T. Moezie
*Attorney, Agent, or Firm*—Arent Fox Kintner Plotkin & Kahn, PLLC

[57] ABSTRACT

A distamycin derivative of formula (I):

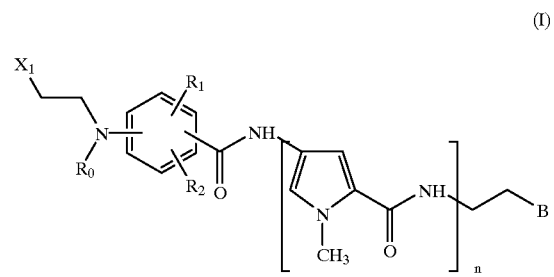

wherein:
n is 2, 3 or 4;
$R_0$ is $C_1$–$C_4$ alkyl or —$CH_2CH_2$—$X_2$, wherein $X_2$ is a halogen atom;
$R_1$ and $R_2$ are selected, each independently, from: hydrogen, $C_1$–$C_4$ alkyl optionally substituted by one or more fluorine atoms, $C_1$–$C_4$ alkoxy, and halogen;
$X_1$ is a halogen atom;
B is selected from:

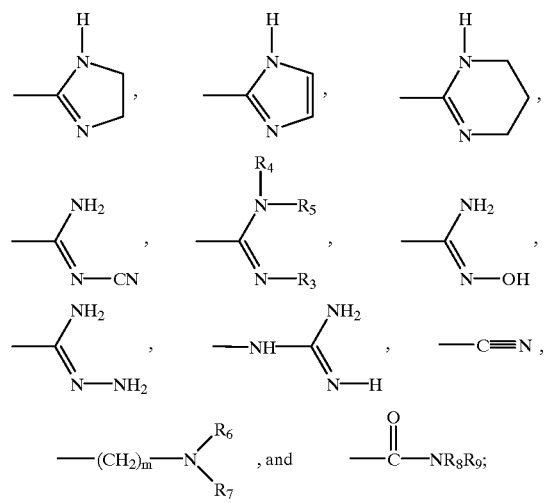

wherein $R_3$, $R_4$, $R_5$, $R_6$, $R_7$, $R_8$, and $R_9$ are, each independently, hydrogen or $C_1$–$C_4$ alkyl, and m is 0, 1 or 2; with the proviso that, when $R_0$ is —$CH_2CH_2$—$X_2$, B is different from —$(CH_2)_m$—$NR_6R_7$ and at least one of $R_3$, $R_4$, and $R_5$ is $C_1$–$C_4$ alkyl;
or a pharmaceutically acceptable salt thereof.

15 Claims, No Drawings

DISTAMYCIN DERIVATIVES, PROCESS FOR PREPARING THEM, AND THEIR USE AS ANTITUMOR AND ANTIVIRAL AGENTS

FIELD OF THE INVENTION

The present invention refers to new alkylating antitumor and antiviral agents related to the known antibiotic distamycin A:

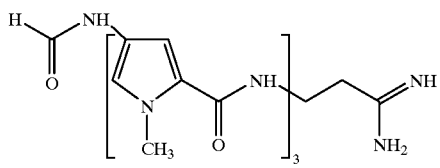

which belongs to the family of the pyrroleamidine antibiotics and is reported to interact reversibly and selectively with DNA-AT sequences interfering with both replication and transcription [Nature, 203, 1064 (1964); FEBS Letters, 7 (1970) 90; Prog.Nucleic Acids Res.Mol.Biol., 15, 285 (1975)].

DE-A-1795539 describes the preparation of distamycin derivatives in which the formyl group of distamycin is replaced by hydrogen or by the acid residue of an organic $C_1$–$C_4$ aliphatic acid or of cyclopentylpropionic acid. EP-B-246,868 describes distamycin analogues in which the distamycin formyl group is substituted by aromatic, alicyclic or heterocyclic moieties bearing alkylating groups.

As alkylating groups, N,N-dihaloethylamino moieties, derived from bifunctional nitrogen mustards, have resulted to be particularly effective. Conversely, it is well known in the literature that mono-functional nitrogen mustards per se (the so-called half mustards) do not show antitumor activity (see e.g. T. J. Bardos, J.Med.Chem. 8, 167 (1965) and references cited therein).

BRIEF SUMMARY OF THE INVENTION

It has now been found that a new class of distamycin derivatives as defined hereinunder, wherein the distamycin formyl group is substituted by a benzoyl moiety bearing as alkylating group a bis-halo-ethylamino moiety (mustard moiety) or a N-alkyl-N-haloethyl-amino group (half mustard moiety), while the amidine group is substituted by various nitrogen-containing end-groups, shows valuable biological properties.

Accordingly, the present invention relates to new distamycin derivatives of formula (I) as defined hereinunder, to a process for preparing them, to pharmaceutical compositions containing them and to their use in therapy, particularly as antitumor and antiviral agents.

The present invention provides a distamycin derivative of formula (I):

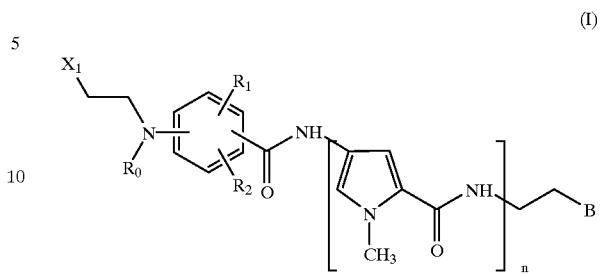

wherein:

n is 2, 3 or 4;

$R_0$ is $C_1$–$C_4$ alkyl or —$CH_2CH_2$—$X_2$, wherein $X_2$ is a halogen atom;

$R_1$ and $R_2$ are selected, each independently, from: hydrogen, $C_1$–$C_4$ alkyl optionally substituted by one or more fluorine atoms, $C_1$–$C_4$ alkoxy, and halogen;

$X_1$ is a halogen atom;

B is selected from:

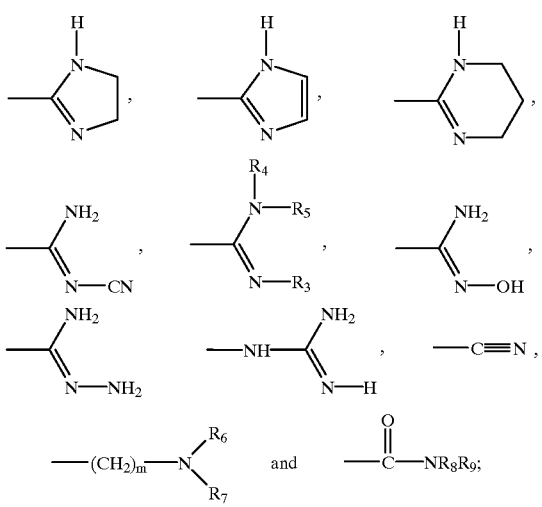

wherein $R_3$, $R_4$, $R_5$, $R_6$, $R_7$, $R_8$, and $R_9$ are, each independently, hydrogen or $C_1$–$C_4$ alkyl, and m is 0, 1 or 2; with the proviso that, when $R_0$ is —$CH_2CH_2$—$X_2$, B is different from —$(CH_2)_m$—$NR_6R_7$ and at least one of $R_3$, $R_4$, and $R_5$ is $C_1$–$C_4$ alkyl;

or a pharmaceutically acceptable salt thereof.

DETAILED DESCRIPTION OF THE INVENTION

The present invention includes within its scope also all the possible isomers covered by formula (I) both separately and in mixture, as well as the metabolites and the pharmaceutically acceptable bio-precursors (otherwise known as pro-drugs) of the compounds of formula (I).

The alkyl and alkoxy groups may have branched or straight chains. A $C_1$–$C_4$ alkyl group is preferably methyl or ethyl, a $C_1$–$C_4$ alkoxy group is preferably methoxy or ethoxy. When substituted by one or more fluorine atoms, a $C_1$–$C_4$ alkyl group is preferably a $C_1$–$C_4$ perfluoroalkyl group, e.g. —$CF_3$. Halogen is preferably fluorine, chlorine or bromine.

In the phenyl ring, the carboxamide moiety and the half-mustard or the mustard moiety are preferably in meta or para position with respect to each other.

As to the $R_1$ and $R_2$ groups, they can be in any of the free positions of the phenyl ring. In a first preferred embodiment $R_1$ is hydrogen, and $R_2$ is hydrogen, $C_1$–$C_4$ alkyl optionally substituted by one or more fluorine atoms, $C_1$–$C_4$ alkoxy, or halogen, preferably fluorine; in a second preferred embodiment both $R_1$ and $R_2$ are, each independently, $C_1$–$C_4$ alkyl optionally substituted by one or more fluorine atoms, $C_1$–$C_4$ alkoxy, or halogen, preferably fluorine. A particularly preferred value of n is 3; $X_1$ and $X_2$ are preferably the same halogen atom, particularly chloro or bromo.

Preferably, $R_3$, $R_4$, $R_5$, $R_6$, $R_7$, $R_8$, and $R_9$ are, each independently, hydrogen, methyl, or ethyl, while $R_0$ is preferably methyl, ethyl, n-propyl, i-propyl, 2-chloroethyl, or 2-bromoethyl.

Pharmaceutically acceptable salts of the compounds of formula (I) are their salts with pharmaceutically acceptable, either inorganic or organic, acids. Examples of inorganic acids are hydrochloric, hydrobromic, sulfuric and nitric acid; examples of organic acids are acetic, propionic, succinic, malonic, citric, tartaric, methanesulfonic and p-toluenesulfonic acid.

A preferred class of compounds according to the present invention is that of formula (I) wherein:

n is 3;
$X_1$ is chloro or bromo;
$R_0$ is methyl, ethyl, n-propyl or i-propyl;
$R_1$ and $R_2$ are, each independently, hydrogen, —$CH_3$, —$OCH_3$, or —$CF_3$;
B is selected from:

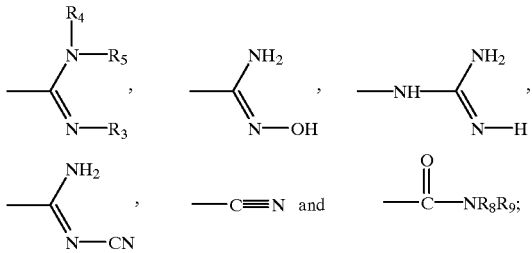

wherein $R_3$, $R_4$, $R_5$, $R_8$ and $R_9$ are, each independently, hydrogen or methyl; or the pharmaceutically acceptable salts thereof.

Another preferred class of compounds according to the present invention is that of formula (I) wherein:
n is 3;
$R_0$ is —$CH_2CH_2$—$X_2$;
$X_1$ and $X_2$ are chloro or bromo;
$R_1$ and $R_2$ are, each independently, hydrogen, —$CH_3$, or —$OCH_3$;
B is selected from:

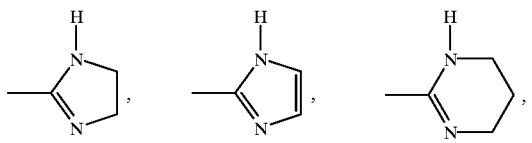

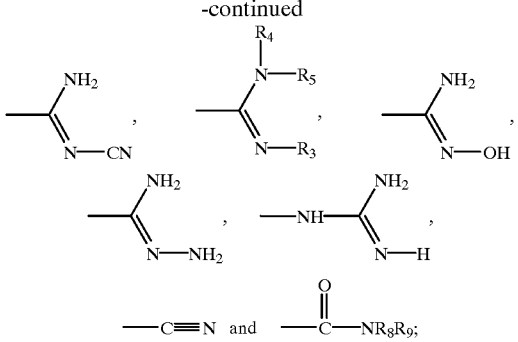

wherein $R_3$, $R_4$, $R_5$, $R_8$ and $R_9$ are, each independently, hydrogen or methyl, with the proviso that at least one of $R_3$, $R_4$, and $R_5$ is methyl;
or the pharmaceutically acceptable salts thereof.

Examples of specific compounds according to the present invention, especially in the form of salts, preferably with hydrochloric or hydrobromic acid, are the following:
1) 3-[1-methyl-4-[1-methyl-4-[1-methyl-4-[4-N-methyl-N-(2-chloroethyl)aminobenzene-1-carboxamido]pyrrole-2-carboxamido]pyrrole-2-carboxamido]pyrrole-2-carboxamido]propionamidine;
2) 3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propionamidine;
3) 3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propionamidine;
4) 3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propionamidine;
5) 3-[1-methyl-4-[1-methyl-4-[1-methyl-4-[3,5-dimethyl-4-N-ethyl-N-(2-chloroethyl)aminobenzene-1-carboxamido]pyrrole-2-carboxamido]pyrrole-2-carboxamido]pyrrole-2-carboxamido]propionamidine;
6) 3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propionamidine;
7) 3-[1-methyl-4-[1-methyl-4-[1-methyl-4-[3-methyl-4-N-ethyl-N-(2-chloroethyl)amino-5-methoxybenzene-1-carboxamido]pyrrole-2-carboxamido]pyrrole-2-carboxamido]pyrrole-2-carboxamido]propionamidine;
8) 3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propionamidine;
9) 3-[1-methyl-4-[1-methyl-4-[1-methyl-4-[3-methyl-4-N-ethyl-N-(2-chloroethyl)amino-5-trifluoromethylbenzene-1-carboxamido]pyrrole-2-carboxamido]pyrrole-2-carboxamido]pyrrole-2-carboxamido]propionamidine;
10) 3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propionamidine;
11) 3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propionamidine;
12) 3-[1-methyl-4-[1-methyl-4-[1-methyl-4-[4-N-ethyl-N-(2-chloroethyl)aminobenzene-1-carboxamido]pyrrole-2- carboxamido]pyrrole-2-carboxamido]pyrrole-2-carboxamido]propion-N-methyl-amidine;

13) 3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propion-N-methyl-amidine;

14) 3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propion-N-methyl-amidine;

15) 3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propion-N-methyl-amidine;

16) 3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propion-N-methyl-amidine;

17) 3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propyl-N-methyl-amidine;

18) 3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propion-N-methyl-amidine;

19) 3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propion-N-methyl-amidine;

20) 3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine;

21) 3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propion-N,N'-dimethyl-amidine;

22) 3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine;

23) 3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine;

24) 3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine;

25) 3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine;

26) 3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propion-N,N'-dimethyl-amidine;

27) 3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propion-N,N'-dimethyl-amidine;

28) 3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propionamidoxime;

29) 3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propionamidoxime;

30) 3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propionamidoxime;

31) 3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propionamidoxime;

32) 3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propionamidoxime;

33) 3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propionamidoxime;

34) 3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propionamidoxime;

35) 3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propionamidoxime;

36) 3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propioncyanamidine;

37) 3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propioncyanamidine;

38) 3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propioncyanamidine;

39) 3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propioncyanamidine;

40) 3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propioncyanamidine;

41) 3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propioncyanamidine;

42) 3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propioncyanamidine;

43) 3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propioncyanamidine;

44) 2-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]ethylguanidine;

45) 2-[1-methyl-4-[1-methyl-4-[1-methyl-4-[4-N-propyl-N-(2-chloroethyl)aminobenzene-1-carboxamido]pyrrole-2- carboxamido]pyrrole-2-carboxamido]pyrrole-2-carboxamido]ethylguanidine;

46) 2-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]ethylguanidine;

47) 2-[1-methyl-4-[1-methyl-4-[1-methyl-4-[3,5-dimethyl-4-N-ethyl-N-(2-chloroethyl)aminobenzene-1-carboxamido]pyrrole-2-carboxamido]pyrrole-2-carboxamido]pyrrole-2-carboxamido]ethylguanidine;

48) 2-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]ethylguanidine;

49) 2-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]ethylguanidine;

50) 2-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]ethylguanidine;

51) 2-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]ethylguanidine;

52) 2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-(2-imidazoline);

53) 2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazoline);

54) 2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)];

55) 2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)];

56) 2-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

57) 2-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

58) 2-[1-methyl-4[1-methyl-4[1-methyl-4[3,5-dimethyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

59) 2-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

60) 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propion-N-methyl-amidine;

61) 3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propion-N-methyl-amidine;

62) 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propion-N,N'-dimethyl-amidine;

63) 3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propion-N,N'-dimethyl-amidine;

64) 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionamidoxime;

65) 3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionamidoxime;

66) 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propioncyanamidine;

67) 3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propioncyanamidine;

68) 3-[1-methyl-4[1-methyl-4[1-methyl-4[3,5-dimethyl-4-N,N-bis(2-chloroethyl)aminobenzene-1-carboxamido]pyrrole-2-carboxamido]pyrrole-2-carboxamido]pyrrole-2-carboxamido]propioncyanamidine;

69) 3-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]propioncyanamidine;

70) 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionamidrazone;

71) 3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionamidrazone;

72) 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionitrile;

73) 3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionitrile;

74) 2-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]ethylguanidine;

75) 2-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]ethylguanidine;

76) 3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propionamide;

77) 3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propionamide;

78) 3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propionamide;

79) 3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propionamide;

80) 3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propionamide;

81) 3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propionamide;

82) 3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propionamide;

83) 3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propionamide;

84) 3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N-methyl-amide;

85) 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionamide;

86) 3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionamide;

87) 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propion-N-methyl-amide;

88) 3-[1-methyl-4[1-methyl-4[1-methyl-4[4-N,N-bis(2-bromoethyl)aminobenzene-1-carboxamido]pyrrole-2-carboxamido]pyrrole-2-carboxamido]pyrrole-2-carboxamido]propionamidoxime;

89) 3-[1-methyl-4[1-methyl-4[1-methyl-4[4-N,N-bis(2-bromoethyl)aminobenzene-1-carboxamido]pyrrole-2-carboxamido]pyrrole-2-carboxamido]pyrrole-2-carboxamido]propion-N,N'-dimethyl-amidine;

90) 3-[1-methyl-4[1-methyl-4[1-methyl-4[4-N,N-bis(2-bromoethyl)aminobenzene-1-carboxamido]pyrrole-2-carboxamido]pyrrole-2-carboxamido]pyrrole-2-carboxamido]propionitrile.

The present invention also provides a process for the preparation of compounds of formula (I), and the salts thereof, which comprises:

(A) (a) reacting a compound of formula (II):

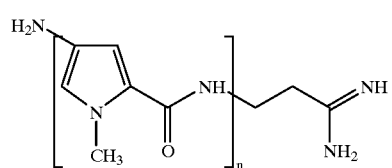

(II)

wherein n is 2, 3 or 4, with a compound of formula (III):

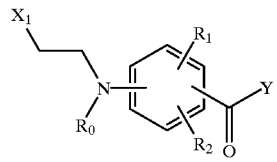

(III)

wherein:

$R_0$ is $C_1$–$C_4$ alkyl or —$CH_2CH_2$—$X_2$, wherein $X_2$ is a halogen atom;

$R_1$ and $R_2$ are selected, each independently, from: hydrogen, $C_1$–$C_4$ alkyl optionally substituted by one or more fluorine atoms, $C_1$–$C_4$ alkoxy, and halogen;

$X_1$ is a halogen atom; and

Y is hydroxy or a leaving group;

to obtain a compound of formula (IV):

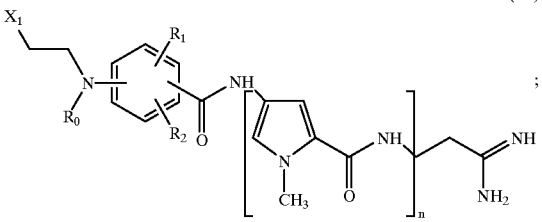

(IV)

and reacting the compound of formula (IV) with:

(i) $H_2N$—$(CH_2)_p$—$NH_2$, where p is 2 or 3, to obtain a compound of formula (I) wherein B is:

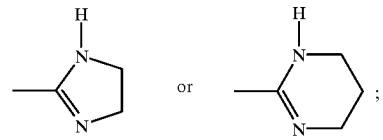

(ii) $H_2N$—$CH_2$—CHO to obtain a compound of formula (I) wherein B is:

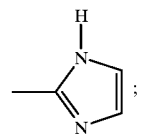

(iii) $H_2N$—CN to obtain a compound of formula (I) wherein B is:

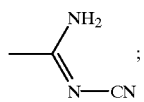

(iv) $H_2N$—OH to obtain a compound of formula (I) wherein B is:

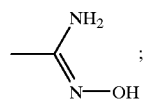

(v) $H_2N-NH_2$ to obtain a compound of formula (I) wherein B is:

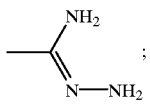

(vi) $HNR_4R_5$ to obtain a compound of formula (I) wherein B is:

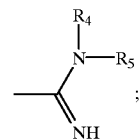

and if necessary reacting the compound of formula (I) thus obtained with $H_2NR_3$, to obtain a compound of formula (I) wherein B is:

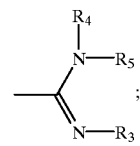

wherein $R_3$, $R_4$, and $R_5$ are, each independently, hydrogen or $C_1-C_4$ alkyl, with the proviso that at least one of $R_3$, $R_4$, and $R_5$ is $C_1-C_4$ alkyl;

(vii) succinic anhydride to obtain a compound of formula (I) wherein B is $-C\equiv N$;

(viii) water in an alkaline medium, to obtain a compound of formula (I) wherein B is $-CO-NR_8R_9$ with $R_8$ and $R_9$ equal to hydrogen; or (ix) $HNR_8R_9$ to obtain a compound of formula (I) wherein B is:

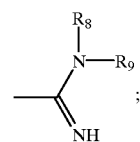

and reacting the compound of formula (I) thus obtained with water in an alkaline medium, to obtain a compound of formula (I) wherein B is $-CO-NR_8R_9$, with $R_8$ and $R_9$, each independently, equal to hydrogen or $C_1-C_4$ alkyl, with the proviso that at least one of $R_8$ and $R_9$ is $C_1-C_4$ alkyl;

or:

(b) reacting a compound of formula (V):

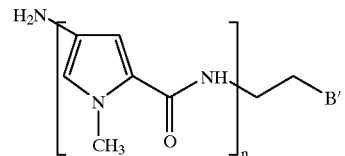

(V)

wherein n is 2, 3 or 4; B' is selected from:

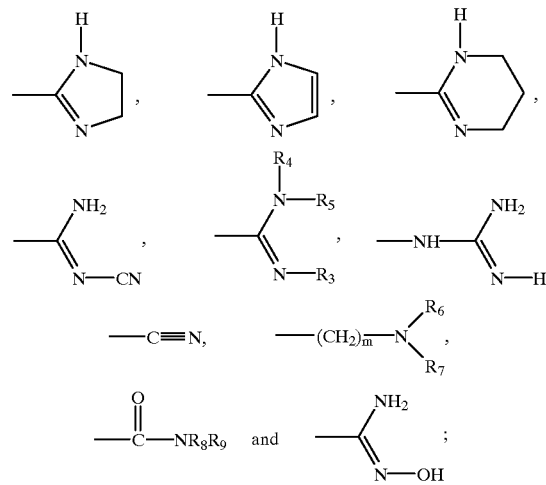

wherein $R_3$, $R_4$, $R_5$, $R_6$, $R_7$, $R_8$ and $R_9$ are each independently hydrogen or $C_1-C_4$ alkyl, and m is 0, 1 or 2;

with a compound of formula (III):

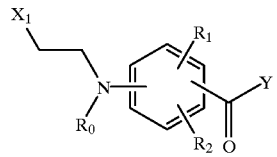

(III)

wherein:
$R_0$ is $C_1-C_4$ alkyl or $-CH_2CH_2-X_2$, wherein $X_2$ is a halogen atom;
$R_1$ and $R_2$ are selected, each independently, from: hydrogen, $C_1-C_4$ alkyl optionally substituted by one or more fluorine atoms, $C_1-C_4$ alkoxy, and halogen;
$X_1$ is a halogen atom; and
Y is hydroxy or a leaving group;
to obtain a compound of formula (I) wherein B is B' as defined above, with the proviso that when $R_0$ is $-CH_2CH_2-X_2$, B and B' are different from $-(CH_2)_m-NR_6R_7$, and at least one of $R_3$, $R_4$, and $R_5$ is $C_1-C_4$ alkyl; and (B) if necessary converting the thus obtained compound of formula (I) into a pharmaceutically acceptable salt thereof.

In formula (III), Y is hydroxy or a leaving group selected, for instance, from chloro, 2,4,5-trichlorophenoxy, 2,4-dinitro-phenoxy, succinimido-N-oxy, imidazolyl group, and the like.

The reaction of a compound of formula (II) (process (a)) or of formula (V) (process (b)) with a compound of formula (III) can be carried out according to known methods, for instance those described in EP-B-246,868.

The reaction between a compound of formula (II) or of formula (V) and a compound of formula (III) wherein Y is hydroxy, is preferably carried out with a molar ratio (II):(III) or (V):(III) of from 1:1 to 1:2, in an organic solvent, such as, e.g., dimethylsulphoxide, hexamethylphosphotriamide, dimethylacetamide, dimethylformamide, ethanol, benzene, or pyridine, in the presence of an organic or inorganic base such as, e.g., triethylamine, diisopropyl ethylamine, or sodium or potassium carbonate or bicarbonate, and of a condensing agent such as, e.g., N-ethyl-N'-(3-dimethylaminopropyl)-carbodiimide, N,N'-dicyclohexyl-carbodiimide, and/or 1-hydroxy-benzotriazole hydrate. The reaction temperature may vary from about −10° C. to about 100° C., and the reaction time from about 1 to about 24 hours.

The reaction between a compound of formula (II) or of formula (V) and a compound of formula (III), wherein Y is a leaving group as defined above, may be carried out with a molar ratio (II):(III) or (V):(III) of from about 1:1 to about 1:2, in an organic solvent, such as, e.g., dimethylformamide, dioxane, pyridine, tetrahydrofurane, or mixtures thereof with water, optionally in the presence of an organic base, e.g. N,N'-diisopropylethylamine, triethylamine, or an inorganic base, e.g. sodium or potassium bicarbonate, at a temperature of from about 0° C. to about 100° C., and for a time varying from about 2 hours to about 48 hours.

The reaction between a compound of formula (IV) and one of the reactants as described at points (i), (ii), (iii), (iv), (v), (vi), or (ix) can be carried out according to known methods, for instance those reported in: U.S. Pat. No. 4,766,142, Chem. Revs. 1961, 155; J. Med. Chem. 1984, 27, 849–857; Chem. Revs. 1970, 151; and "The Chemistry of Amidines and Imidates", edited by S. Patai, John Wiley & Sons, N.Y. (1975).

The reaction of a compound of formula (IV) with succinic anhydride (see point (vii) above) is preferably carried out with a molar ratio (IV):succinic anhydride of from 1:1 to 1:3 in an organic solvent such as, e.g., dimethyl sulphoxide, dimethylformamide, in the presence of an organic or inorganic base such as, e.g., triethylamine, diisopropylethylamine, sodium or potassium carbonate, and the like. The reaction temperature may vary from about 25° C. to about 100° C., and the reaction time from about 1 hour to about 12 hours.

The reaction with water in an alkaline medium (see points (viii) and (ix) above) may be carried out according to known methods usually employed for an alkaline hydrolysis, e.g. by treating the substrate with an excess of sodium or potassium hydroxide dissolved in water or in a mixture of water with an organic solvent, e.g. dioxane, tetrahydrofurane, or acetonitrile, at a temperature of from about 50° to about 100° C., for a time varying from about 2 hours to about 48 hours.

The compounds of formula (II) are known compounds or may be prepared by known methods from known compounds: see, for instance, Arcamone et al. Gazzetta Chim. Ital. 97, 1097 (1967). The compounds of formula (III) are known compounds too or may be prepared starting from known compounds through reactions well known in organic chemistry: see, for instance, J. Med. Chem. 9, 882 (1966), J. Med. Chem. 25, 178 (1982), J. Org. Chem. 26, 4996 (1961), J. Heterocyclic Chem. 32, 1063 (1995), Synth. Commun. 24, 3129–3134 (1994).

The compounds of formula (V) are known compounds, or can be obtained by known methods (see e.g. Tetrahedron Letters 31, 1299 (1990), Anticancer Drug Design 9, 511 (1994)), such as:

(i) by hydrolytic deformylation, in a basic or acid medium, of compounds of formula (VI):

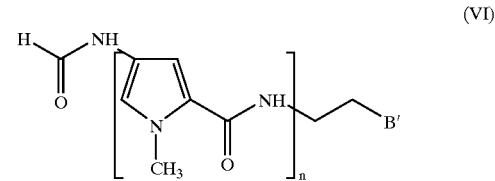

(ii) by nitro-group reduction, according to known methods, of compounds of formula (VII):

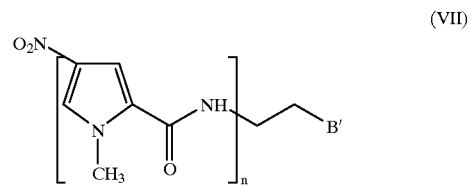

wherein B' is selected from:

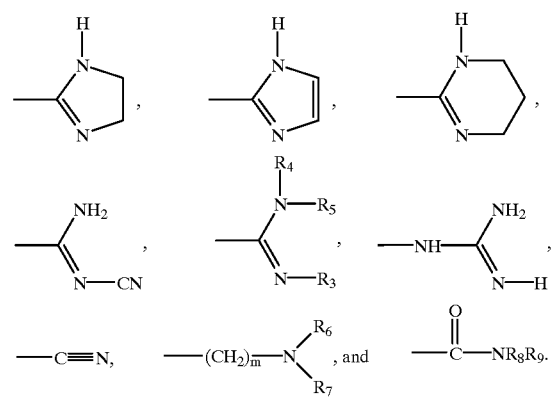

The compounds of formula (VI), except when B' is equal to

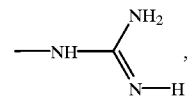

can in turn be prepared starting from distamycin compounds of formula (VIII):

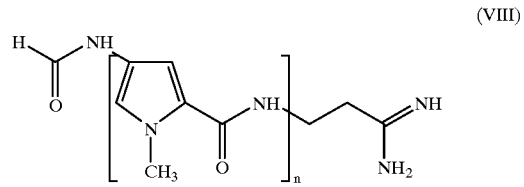

using the same reactants as reported in the second step of process (a).

The compounds of formula (VII) can be obtained:
(i) from a compound of formula (IX):

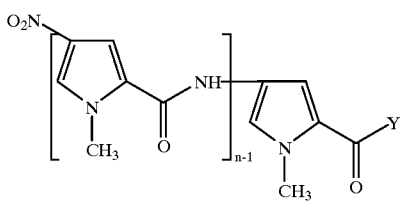

wherein n and Y are as defined above, by reaction with a compound of formula:

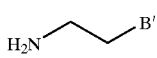

wherein B' is selected from:

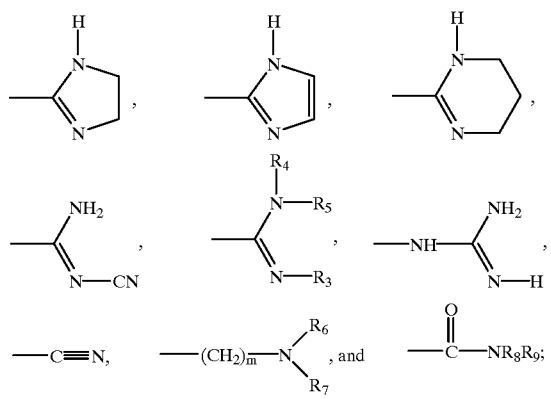

(ii) except when B' is equal to

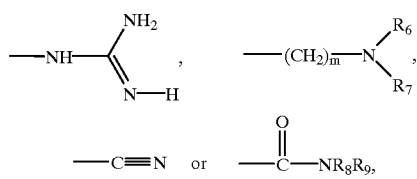

by Pinner reaction of a compound of formula:

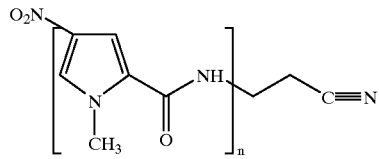

with a suitable amine compound as defined at point (i), (ii), (iii), or (vi) above.

In the above reaction (i), when at least one of $R_6$ and $R_7$ is hydrogen, the amine group may be protected by a suitable protecting group (e.g. benzyl, carbobenzyloxy, and the like).

The compounds of formulas (VIII), (IX), (X) and (XI) are known compounds, or may be obtained by known methods (see e.g. Tetrahedron, 34, 2389–2391, 1978; J. Org. Chem., 46, 3492–3497, 1981).

Salification of a compound of formula (I), as well as preparation of a free compound starting from a salt, may be carried out by known standard methods.

Well known procedures such as, e.g., fractional crystallization or chromatography, may also be followed for separating a mixture of isomers of formula (I) into the single isomers.

The compounds of formula (I) may be purified by conventional techniques such as, e.g., silica gel or alumina column chromatography, and/or by recrystallization from an organic solvent such as, e.g., a lower aliphatic alcohol, e.g. methyl, ethyl or isopropyl alcohol, or dimethylformamide.

PHARMACOLOGY

The compounds of formula (I) or pharmaceutically acceptable salts are useful as antineoplastic and/or antiviral agents. Particularly, they show cytostatic properties towards tumor cells, so that they can be useful to inhibit growth of various tumors in mammals, including humans, such as, for instance, carcinomas, e.g. mammary carcinoma, lung carcinoma, bladder carcinoma, colon carcinoma, ovary and endometrial tumors. Other neoplasias in which the compounds of the present invention can find application are, for instance, sarcomas, e.g. soft tissue and bone sarcomas, and the hematological malignancies such as, e.g. leukemias.

The in vitro antitumor activity was evaluated by cytotoxicity studies carried out on murine $L_{1210}$ leukemia cells. Cells were derived from in vivo tumors and established in cell culture. Cells were used until the tenth passage. Cytotoxicity was determined by counting surviving cells after 48 hours treatment.

The percentage of cell growth in the treated cultures was compared with that of controls. $IC_{50}$ values (concentration inhibiting 50% of the cellular growth in respect to controls) were calculated on dose-response.

The compounds of the invention were tested also in vivo on $L_{1210}$ murine leukemia and on murine reticulosarcoma M 5076 with the following procedure.

$L_{1210}$ murine leukemia was maintained in vivo by i.v. serial transplantation. For experiments, $10^5$ cells were injected i.p. in CD2F1 female mice, obtained from Charles River Italy. Animals were 8 to 10 weeks old at the beginning of the experiments. Compounds were administered i.v. at day +1 after tumor cells injections.

M5076 reticulosarcoma was maintained in vivo by i.m. serial transplantation. For experiments, $5 \times 10^5$ cells were injected i.m. in C57B16 female mice, obtained from Charles River Italy. Animals were 8 to 10 weeks old at the beginning of the experiments. Compounds were administered i.v. at day 3, 7 and 11 after tumor injection.

Survival time of mice and tumor growth were calculated and activity was expressed in term of T/C % and T.I. %.

$$T/C = \frac{\text{median survival time treated group}}{\text{median survival time untreated group}} \times 100$$

T.I.=% inhibition of tumor growth respect to control

Tox: number of mice which died for toxicity.

Tox determination was made when mice died before the control and/or tested significant body weight loss and/or spleen and/or liver size reduction were observed.

The compounds of the invention show also a remarkable effectiveness in interfering with the reproductive activity of pathogenic viruses and protect tissue cells from viral infections. For example, they show activity against DNA viruses such as, for instance, herpes, e.g. herpes simplex and herpes zoster viruses, virus vaccinia, RNA viruses such as, e.g., Rhinovirus and Adenovirus, and against retroviruses such as, for instance, sarcoma viruses, e.g., murine sarcoma virus, and leukemia viruses, e.g. Friend leukemia virus.

For example, effectiveness against herpes, coxsackie and respiratory syncytial viruses was tested in a fluid medium as follows. Serial two-fold dilutions of the compounds from 200 to 1.5 mcg/ml were distributed in duplicate 0.1 ml/well in 96 well microplates for tissue culture. Cell suspensions ($2 \times 10^5$ cells/ml) infected with about $5 \times 10^{-3}$ $TCID_{50}$ of virus/cell were immediately added 0.1 ml/well.

After 3–5 day incubation at 37° C. in $CO_2$ 5%, the cell cultures were evaluated by microscope observation and Minimum Inhibiting Concentration (MIC) was determined, MIC being the minimum concentration which determines a reduction of cytopathic effect in comparison with the infected controls.

The compounds of the invention can be administered to mammals, including humans, through the usual routes, for example, parenterally, e.g. by intravenous injection or infusion, intramuscularly, subcutaneously, topically or orally. The dosage depends on the age, weight and conditions of the patient and on the administration route. For example, a suitable dosage for administration to adult humans may range from about 0.1 to about 150–200 mg pro dose 1–4 times a day.

The present invention further provides a pharmaceutical composition, which comprises a compound of formula (I) or a pharmaceutically acceptable salt thereof as an active principle, in association with one or more pharmaceutically acceptable carriers and/or diluents.

The pharmaceutical compositions of the present invention are usually prepared following conventional methods and are administered in a pharmaceutically suitable form. For instance, solutions for intravenous injection or infusion may contain as a carrier, for example, sterile water or preferably, they may be in the form of sterile aqueous isotonic saline solutions.

Suspensions or solutions for intramuscular injections may contain, together with the active compound a pharmaceutically acceptable carrier, e.g. sterile water, olive oil, ethyl oleate, glycols, e.g. propylene glycol, and if desired, a suitable amount of lidocaine hydrochloride.

In the forms for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulation. Said pharmaceutical preparation may be manufactered by known techniques, for example by means of mixing, granulating, tabletting, sugar-coating or film-coating processes.

The present invention also provides a compound of formula (I) or a pharmaceutically acceptable salt thereof for use in a method of treating the human or animal body by therapy. Furthermore, the present invention provides a method for treating tumors and viral infections in a patient in need of it, which comprises administering to said patient a composition of the invention.

A further object of the present invention is a combined method for treating cancer or for ameliorating the conditions of mammals, including humans, suffering from cancer, said method comprising administering a compound of formula (I), or a pharmaceutically acceptable salt thereof, and an additional antitumor agent, close enough in time and in amounts sufficient to produce a therapeutically useful effect.

The present invention also provides products containing a compound of formula (I), or a pharmaceutically acceptable salt thereof, and an additional antitumour agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice. Examples of antitumor agents that can be formulated with a compound of formula (I), or alternatively, can be administered in a combined method of treatment, include doxorubicin, daunomycin, epirubicin, idarubicin, etoposide, fluoro-uracil, melphalan, cyclophosphamide, 4-demethoxy daunorubicin, bleomycin, vinblastin, and mitomycin, or mixtures thereof.

The following examples are given to better illustrate the invention, but do not limit the scope of the invention itself.

EXAMPLE 1

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propionamidine hydrochloride Step I The Intermediate Ethyl N-ethyl-4-aminobenzoate To a solution of 5 g of ethyl 4-aminobenzoate in 100 ml of methanol, 0.74 ml of acetaldehyde, 1.89 g of sodium cyanoborohydride and 2.1 ml of hydrochloric acid 23% were added.

The solution was stirred at room temperature for one day, then the solvent evaporated in vacuo and the crude residue purified by flash chromatography (n-exane/ethyl acetate 9/1) to yield 2 g of intermediate as a white solid.

EI-MS: m/z 193(80, M$^{+\bullet}$); other fragment radicals 178; 150; 148

PMR (CDCl$_3$) δ: 7.91 (m, 2H), 6.55 (m, 2H), 4.32 (q, J=7.1 Hz, 2H), 4.05 (b.s., 1H), 3.21 (m, 2H), 1.34 (t, J=7.1 Hz, 3H), 1.25 (t, J=7.1 Hz, 3H)

By analogous procedure and using the suitable starting materials the following intermediates can be obtained:
ethyl N-methyl-4-aminobenzoate;
ethyl N-propyl-4-aminobenzoate
PMR (CDCl$_3$) δ: 7.87 (m, 2H), 6.53 (m, 2H), 4.31 (q, J=7.1 Hz, 2H), 4.10(b.s., 1H), 3.16 (t, J=7.2 Hz, 2H), 1.65 (m, 2H), 1.37 (t, J=7.1 Hz, 3H), 1.03 (t, J=7.1 Hz, 3H);
ethyl 3-methyl-N-ethyl-4-aminobenzoate
PMR (CDCl$_3$) δ: 7.85 (m, 1H), 7.79 (m, 1H), 6.54 (d, J=8.3 Hz, 1H), 4.29 (q, J=7.1 Hz, 2H), 3.82 (b.s., 1H), 3.24 (q, J=7.1 Hz, 2H), 2.13 (s, 3H), 1.35 (t, J=7.1 Hz, 3H), 1.30 (t, J=7.1 Hz, 3H);

ethyl 3,5-dimethyl-N-ethyl-4-aminobenzoate;
ethyl 3-methoxy-N-ethyl-4-aminobenzoate;
ethyl 3-methyl-N-ethyl-4-amino-5-methoxybenzoate;
ethyl 3-trifluoromethyl-N-ethyl-4-aminobenzoate; and
ethyl 3-methyl-N-ethyl-4-amino-5-trifluoromethylbenzoate;

Step II

The Intermediate 4-N-ethyl-N-(2-chloroethyl) aminobenzoic acid

To a solution of 2 g of the intermediate obtained from step I in 60 ml of methanol, 4 ml of chloroacetaldehyde (40% in water), 782 mg of sodium cyanoborohydride and 1 ml of hydrochloric acid 23% were added.

The solution was stirred at room temperature for four hours then the solvent evaporated in vacuo and the crude residue purified by flash chromatography (n-exane/ethyl acetate 9/1) to yield 2 g of ethyl 4-N-ethyl-N-(2-chloroethyl) aminobenzoate as a yellow oil which was dissolved in 20 ml of 37% hydrochloric acid and refluxed for two hours. The mixture was extracted with ethyl acetate (3×100 ml), the combined organic extracts were washed with water (20 ml), dried on sodium sulfate and concentrated in vacuo to yield 1.8 g of the intermediate as a white solid.

EI-MS: m/z 227(20, M$^{+\bullet}$); other fragment radicals 178; 150

PMR (CDCl$_3$) δ: 11.05 (b.s. 1H), 7.96 (m, 2H), 6.65 (m, 2H), 3.64 (m, 4H), 3.51 (q, J=7.1 Hz, 2H), 1.20 (t, J=7.1 Hz, 3H).

By analogous procedure and using the suitable starting materials the following products can be obtained:
4-N-methyl-N-(2-chloroethyl)aminobenzoic acid;
4-N-propyl-N-(2-chloroethyl)aminobenzoic acid
PMR (CDCl$_3$) δ: 12.00 (b.s. 1H), 7.94 (m, 2H), 6.66 (m, 2H), 3.18 (m, 4H), 3.34 (t, J=7.2 Hz, 2H), 1.67 (m, 2H), 0.96 (t, J=7.1 Hz, 3H);
3-methyl-4-N-ethyl-N-(2-chloroethyl)aminobenzoic acid
PMR (CDCl$_3$) δ: 11.00 (b.s. 1H), 7.93 (m, 1H), 7.89 (m, 1H), 7.10 (d, J=8.3 Hz, 1H), 3.48 (m, 4H), 3.12 (q, J=7.1 Hz, 2H), 2.36 (s, 3H), 1.08 (t, J=7.1 Hz, 3H);
3,5-dimethyl-4-N-ethyl-N-(2-chloroethyl)aminobenzoic acid;
3-methyl-4-N-ethyl-N-(2-chloroethyl)amino-5-methoxybenzoic acid;
3-trifluoromethyl-4-N-ethyl-N-(2-chloroethyl) aminobenzoic acid;
3-methyl-4-N-ethyl-N-(2-chloroethyl)amino-5-trifluoromethylbenzoic acid;
4-N-methyl-N-(2-bromoethyl)aminobenzoic acid; and
3-methyl-4-N-methyl-N-(2-bromoethyl)aminobenzoic acid.

Step III

The Intermediate 4-N-ethyl-N-(2-chloroethyl) aminobenzoyl-1-imidazole

A solution of 600 mg of the intermediate obtained from step II and 580 mg of 1,1'-carbonyldiimidazole in 30 ml of ethyl acetate was stirred at room temperature for three hours. The solvent was evaporated in vacuo and the crude residue purified by flash chromatography (ethyl acetate/n-exane: 7/3) to yield 700 mg of the intermediate as a yellow oil.

EI-MS: m/z 277(10, M$^{+\bullet}$); other fragment radicals 228; 210

PMR (CDCl$_3$) δ: 8.07 (m, 1H), 7.72 (m, 2H), 7.50 (m, 1H), 7.12 (m, 1H), 6.71 (m, 2H), 3.69 (m, 4H), 3.51 (q, J=7.1 Hz, 2H), 1.22 (t, J=7.1 Hz, 3H)

By analogous procedure and using the suitable starting materials the following products can be obtained:
4-N-methyl-N-(2-chloroethyl)aminobenzoyl-1-imidazole;
4-N-propyl-N-(2-chloroethyl)aminobenzoyl-1-imidazole;
3-methyl-4-N-methyl-N-(2-chloroethyl)aminobenzoyl-1-imidazole;
3,5-dimethyl-4-N-ethyl-N-(2-chloroethyl)aminobenzoyl-1-imidazole;
3-methyl-4-N-ethyl-N-(2-chloroethyl)amino-5-methoxybenzoyl-1-imidazole;
3-trifluoromethyl-4-N-ethyl-N-(2-chloroethyl) aminobenzoyl-1-imidazole;
3-methyl-4-N-ethyl-N-(2-chloroethyl)amino-5-trifluoromethylbenzoyl-1-imidazole;
4-N-methyl-N-(2-bromoethyl)aminobenzoyl-1-imidazole; and
3-methyl-4-N-methyl-N-(2-bromoethyl)aminobenzoyl-1-imidazole.

Step IV

The Title Compound

A solution of 390 mg of the intermediate obtained from step III, 95 mg of imidazole and 738 mg of 3-[1-methyl-4-[1-methyl-4-[1-methyl-4-aminopyrrole-2-carboxamido]pyrrole-2-carboxamido]pyrrole-2-carboxamido] propionamidine dihydrochloride (prepared as reported in J.Med.Chem 32,774–778,1989) in 20 ml of DMF was stirred at room temperature for three hours.

The solvent was evaporated in vacuo and the crude residue purified by flash chromatography (methylene chloride/methanol: 8/2) to yield 400 mg of the title compound as a yellow solid.

FAB-MS: m/z 663 (35, [M+H]$^+$); 210

U.V. (EtOH 95%) $\lambda_{max}$=316.8, $\epsilon$=55902

PMR (DMSO-d$_6$) δ: 9.96 (s, 3H), 9.93 (s, 1H), 9.90 (s, 1H), 8.98 (b.s., 2H), 8.65 (b.s., 2H), 8.21 (t, J=5.9 Hz, 1H), 7.82 (m, 2H), 7.27 (d, J=1.7 Hz, 1H), 7.22(d, J=1.7 Hz, 1H), 7.17 (d, J=1.7 Hz, 1H), 7.07 (d, J=1.7 Hz, 1H), 7.05 (d, J=1.7 Hz, 1H), 6.94 (d, J=1.7 Hz, 1H), 6.75 (m, 2H), 3.85 (s, 3H), 3.83 (s, 3H), 3.80 (S, 3H), 3.72 (m, 2H), 3.47 (m, 2H), 2.62 (m, 2H), 1.10 (t, J=6.9 Hz, 3H).

By analogous procedure and using the suitable starting materials the following products can be obtained:
3-[1-methyl-4-[1-methyl-4-[1-methyl-4-[4-N-methyl-N-(2-chloroethyl)aminobenzene-1-carboxamido]pyrrole-2-carboxamido]pyrrole-2-carboxamido]pyrrole-2-carboxamido]propionamidine hydrochloride;
3-[1-methyl-4-[1-methyl-4-[1-methyl-4-[3-methyl-4-N-ethyl-N-(2-chloroethyl)aminobenzene-1-carboxamido] pyrrole-2-carboxamido]pyrrole-2-carboxamido]pyrrole-2-carboxamido]propionamidine hydrochloride
FAB-MS: m/z 677 (15, [M+H]$^+$)
U.V. (EtOH 95%) $\lambda_{max}$=311.8, $\epsilon$=44747.
PMR (DMSO-d$_6$) δ: 10.19 (s, 1H), 9.99 (s, 1H), 9.93 (s, 1H), 8.98 (b.s., 2H), 8.63 (b.s., 2H), 8.23 (t, J=5.7 Hz, 1H), 7.80 (m, 1H), 7.76 (m, 1H), 7.31 (d, J=1.8 Hz, 1H), 7.25 (d, J=1.8 Hz, 1H), 7.21 (d, J=8.3 Hz, 1H), 7.19 (d, J=1.8 Hz, 1H) 7.10 (d, J=1.8 Hz, 1H), 7.07 (d, J=1.8 Hz, 1H), 6.96 (d, J=1.8 Hz, 1H), 3.86 (s, 3H), 3.84 (s, 3H), 3.81 (s, 3H), 3.57 (m, 2H), 3.50 (m, 4H), 3.09 (q, J=7.1 Hz, 2H), 2.62 (t, J=6.5 Hz, 2H), 2.31 (s, 3 H), 0.95 (t, J=7.1 Hz, 3H);
3-[1-methyl-4-[1-methyl-4-[1-methyl-4-[3,5-dimethyl-4-N-ethyl-N-(2-chloroethyl)aminobenzene-1-carboxamido] pyrrole-2-carboxamido]pyrrole-2-carboxamido]pyrrole-2-carboxamido]propionamidine hydrochloride;

3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propionamidine hydrobromride;

3-[1-methyl-4-[1-methyl-4-[1-methyl-4-[3-methyl-4-N-ethyl-N-2-bromoethyl)aminobenzene-1-carboxamido]pyrrole-2-carboxamido]pyrrole-2-carboxamido]pyrrole-2-carboxamido]propionamidine hydrobromide;

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propionamidoxime;

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N-methyl-amidine hydrochloride;

3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine hydrochloride;

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propioncyanamidine; and 2-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]ethylguanidine hydrochloride.

EXAMPLE 2

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propionamidine hydrochloride A solution of 400 mg of 4-N-propyl-N-(2-chloroethyl)aminobenzoic acid (prepared as reported in example 1 step II) 1 ml of thionyl chloride in 20 ml of benzene was refluxed for two hours, then the solvent was evaporated in vacuo. The crude residue was dissolved in 10 ml dioxane and added in small portions to a solution of 200 mg of 3-[1-methyl-4-[1-methyl-4-[1-methyl-4-aminopyrrole-2-carboxamido]pyrrole-2-carboxamido]pyrrole-2-carboxamido]propionamidine dihydrochloride (prepared as reported in J.Med.Chem 32,774–778,1989) and 125 mg of potassium bicarbonate in 5 ml of water.

The mixture was stirred at room temperature for one hour, the solvent was evaporated in vacuo and the crude residue purified by flash chromatography (methylene chloride/methanol: 8/2) to yield 140 mg of the title compound.

FAB-MS: m/z 677 (20, [M+H]$^+$)

U.V. (EtOH 95%) $\lambda_{max}$=316.8, $\epsilon$=56327

PMR (DMSO-d$_6$) $\delta$: 9.99 (s, 1H), 9.96 (s, 1H), 9.93 (s, 1H), 9.01 (b.s., 2H), 8.69 (b.s., 2H), 8.24 (t, J=5.4 Hz, 1H), 7.83 (m, 2H), 7.30 (d, J=1.6 Hz, 1H), 7.24 (d, J=1.6 Hz, 1H), 7.19 (d, J=1.6 Hz, 1H) 7.08 (d, J=1.6 Hz, 1H), 7.06 (d, J=1.7 Hz, 1H), 6.95 (d, J=1.7 Hz, 1H), 6.74 (m, 2H), 3.85 (s, 3H), 3.84 (s, 3H), 3.81 (s, 3H), 3.73 (m, 6H), 3.37 (m, 2H), 2.62 (t, J=6.5 Hz, 2H), 1.54 (m, 2H), 0.98 (t, J=7.2 Hz, 3H).

By analogous procedure and using the suitable starting materials the following products can be obtained:

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propionamidine hydrochloride;

3-[1-methyl-4-[1-methyl-4-[3-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propionamidine hydrochloride;

3-[1-methyl-4-[1-methyl-4-[1-methyl-4-[3-methyl-4-N-ethyl-N-(2-chloroethyl)amino-5-methoxybenzene-1-carboxamido]pyrrole-2-carboxamido]pyrrole-2-carboxamido]pyrrole-2-carboxamido]propionamidine hydrochloride;

3-[1-methyl-4-[1-methyl-4-[1-methyl-4-[3-methyl-4-N-ethyl-N-(2-chloroethyl)amino-5-trifluoromethylbenzene-1-carboxamido]pyrrole-2-carboxamido]pyrrole-2-carboxamido]pyrrole-2-carboxamido]propionamidine hydrochloride; and 3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propionamidine hydrochloride.

EXAMPLE 3

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N-methyl-amidine hydrochloride

Step I

The Intermediate 3-[1-methyl-4-[1-methyl-4-[1-methyl-4-aminopyrrole-2-carboxamido]pyrrole-2-carboxamido]pyrrole-2-carboxamido]propion-N-methyl-amidine dihydrochloride A solution of 2 g of distamycin A in 50 ml DMF was treated with 0.38 ml of methylamine hydrochloride 80%. After 8 hours additional 0.25 equivalents of methylamine hydrochloride 80% were added. The solution was evaporated to dryness and the crude residue was purified by flash chromatography (methylene chloride/methanol: 8/2) to give 1.5 g of 3-[1-methyl-4-[1-methyl-4-[1-methyl-4-formamidopyrrole-2-carboxamido]pyrrole-2-carboxamido]pyrrole-2-carboxamido]propion-N-methyl-amidine hydrochloride which was dissolved in 40 ml of methanol and added with 5 ml of 2 N hydrochloric acid.

The reaction was stirred at room temperature for two days, the solvent, evaporated in vacuo and the solid residue suspended in 200 ml of ethyl acetate, yielding after filtration 1.4 g of the intermediate.

FAB-MS: m/z 468 (40, [M+H]$^+$)

PMR (DMSO-d$_6$) $\delta$: 10.20 (s, 3H), 10.18 (s, 1H), 9.98 (s, 1H), 9.65 (m, 1H), 9.20 (s, 1H), 8.63(s, 1H), 8.25 (t, J=5.8 Hz, 1H), 7.25 (d, J=1.7 Hz, 1H), 7.19 (d, J=1.7 Hz, 1H), 7.11 (d, J=1.7 Hz, 1H) 7.08 (d, J=1.7 Hz, 1H), 7.05 (d, J=1.7 Hz, 1H), 6.91 (d, J=1.7 Hz, 1H), 3.90 (s, 3H), 3.85 (s, 3H), 3.79 (s, 3H), 3.60–3.40 (m, 2H), 2.80 (d, J=6 Hz, 3H), 2.61 (m, 2H).

Step II

The Title Compound

A solution of 270 mg of 4-N-ethyl-N-(2-chloroethyl)aminobenzoic acid (prepared as reported in example 1 step II), 1 ml of thionyl chloride in 20 ml of benzene was refluxed for two hours, then solvent evaporated in vacuo. The crude residue was dissolved in 10 ml dioxane and added in small portions to a solution of 200 mg of intermediate obtained from step I and 248 mg of potassium bicarbonate in 10 ml of water.

The mixture was stirred at room temperature for one hour, the solvent was evaporated in vacuo and the crude residue purified by flash chromatography (methylene chloride/methanol: 8/2) to yield 100 mg of the title compound.

FAB-MS: m/z 677 (20, [M+H]$^+$)

U.V. (EtOH 95%) $\lambda_{max}$=317, $\epsilon$=58450

PMR (DMSO-d$_6$) δ: 9.99 (s, 1H), 9.96 (s, 1H), 9.94 (s, 1H), 9.50 (b.s., 1H), 9.15 (b.s., 1H), 9.60 (b.s., 1H), 8.24 (t, J=5.3 Hz, 1H), 7.83 (m, 2H); 7.30 (d, J=1.6 Hz, 1H), 7.24 (d, J=1.6 Hz, 1H), 7.19 (d, J=1.6 Hz, 1H), 7.08 (d, J=1.6 Hz, 1H), 7.06 (d, J=1.6 Hz, 1H), 6.94 (d, J=1.6 Hz, 1H), 6.75 (m, 2H), 3.85 (s, 3H), 3.84 (s, 3H), 3.80 (s, 3H), 3.71 (m, 4H), 3.60–3.40 (m, 4H), 2.79 (s, 3H), 2.60 (m, 2H), 1.17 (t, J=6.8 Hz, 3H).

By analogous procedure and using the suitable starting materials the following products can be obtained:

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propion-N-methyl-amidine hydrochloride;

3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propion-N-methyl-amidine hydrochloride;

3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propion-N-methyl-amidine hydrochloride;

3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propion-N-methyl-amidine hydrochloride;

3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propyl-N-methyl-amidine hydrochloride;

3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propion-N-methyl-amidine hydrobromide;

3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propion-N-methyl-amidine hydrobromide;

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine hydrochloride;

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propion-N,N'-dimethyl-amidine hydrochloride; and 3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propioncyanamidine.

EXAMPLE 4

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine hydrochloride

Step I

The Intermediate 3-[1-methyl-4-[1-methyl-4-[1-methyl-4-aminopyrrole-2-carboxamido]pyrrole-2-carboxamido]pyrrole-2-carboxamido]propion-N,N'-dimethyl-amidine dihydrochloride A solution of 1.5 g of distamycin A in 40 ml DMF was heated to 80° C. and treated with 4 ml of methylamine hydrochloride 80%. After 4 hours additional 5 equivalents (4 ml) of methylamine hydrochloride 80% were added. The solution was evaporated to dryness and the crude residue was purified by flash chromatography (methylene chloride/methanol: 8/2) to yield 1.2 g of 3-[1-methyl-4-[1-methyl-4-[1-methyl-4-formamidopyrrole-2-carboxamido]pyrrole-2-carboxamido]pyrrole-2-carboxamido]propion-N,N'-dimethyl-amidine hydrochloride which was dissolved in 40 ml of methanol and added with 5 ml of 2 N hydrochloric acid solution.

The reaction was stirred at room temperature for two days, the solvent evaporated in vacuo and the solid residue suspended in 200 ml of ethyl acetate, yielding after filtration 1.4 g of the intermediate.

FAB-MS: m/z 482 (45, [M+H]$^+$)

PMR (DMSO-d$_6$) δ: 10.21 (s, 3H), 10.18 (s, 1H), 9.98 (s, 1H), 9.61 (m, 1H), 8.85 (s, 1H), 8.39 (t, J=5.8 Hz, 1H), 8.00–7.70 (b.s., 1H), 7.28 (d, J=1.7 Hz, 1H), 7.22 (d, J=1.7 Hz, 1H), 7.12 (d, J=1.7 Hz, 1H) 7.08 (d, J=1.7 Hz, 1H), 7.03 (d, J=1.7 Hz, 1H), 6.92 (d, J=1.7 Hz, 1H), 3.92 (s, 3H), 3.89 (s, 3H), 3.86 (s, 3H), 3.60–3.40 (m, 2H), 3.02 (d, J=6 Hz, 3H), 2.80 (d, J=6 Hz, 3H), 2.72 (m, 2H).

Step II

The Title Compound

A solution of 110 mg of 4-N-ethyl-N-(2-chloroethyl)aminobenzoic acid (prepared as reported in Example 1, step II), 100 mg of dicyclohexylcarbodiimide and 65 mg of 1-hydroxybenzotriazole hydrate in 15 ml of DMF was stirred at 80° C. for four hours, cooled to room temperature and then added with 180 mg of the intermediate obtained from step I and 128 mg of potassium bicarbonate.

The mixture was stirred at room temperature for 3 hours, the solvent was evaporated in vacuo and the crude residue purified by flash chromatography (methylene chloride/methanol: 8/2) to yield 100 mg of the title compound.

FAB-MS: m/z 691 (25, [M+H]$^+$)

PMR (DMSO-d$_6$) δ: 9.96 (s, 1H), 9.94 (s, 1H), 9.92 (s, 1H), 9.35 (b.s., 1H), 8.50 (b.s., 1H), 8.26 (t, J=5.6Hz, 1H), 7.42 (m, 2H), 7.27 (d, J=1.6Hz, 1H), 7.21 (d, J=1.6Hz, 1H), 7.17 (d, J=1.6Hz, 1H), 7.05 (d, J=1.6Hz, 1H), 6.95 (d, J=1.6Hz, 1H), 6.92 (d, J=1.6Hz, 1H), 6.73 (m, 2H), 3.83 (s, 3H), 3.81 (s, 3H), 3.79 (s, 3H), 3.72 (m, 4H), 3.55–3.35 (m, 4H), 3.01 (s, 3H), 2.76 (s, 3H), 2.61 (m, 2H), 1.61 (t, J=6.8 Hz, 3H).

By analogous procedure and using the suitable starting material the following products can be obtained:

3-[1-methyl-4-[1-methyl-4-[1-methyl-4-[4-N-propyl-N-(2-chloroethyl)aminobenzene-1-carboxamido]pyrrole-2- carboxamido]pyrrole-2-carboxamido]pyrrole-2-carboxamido]propion-N,N'-dimethyl-amidine hydrochloride;

3-[1-methyl-4-[1-methyl-4-[1-methyl-4-[3-methyl-4-N-ethyl-N-(2-chloroethyl)aminobenzene-1-carboxamido] pyrrole-2-carboxamido]pyrrole-2-carboxamido]pyrrole-2-carboxamido]propion-N,N'-dimethyl-amidine hydrochloride;

3-[1-methyl-4-[1-methyl-4-[1-methyl-4-[3,5-dimetyl-4-N-ethyl-N-(2-chloroethyl)aminobenzene-1-carboxamido] pyrrole-2-carboxamido]pyrrole-2-carboxamido]pyrrole-2-carboxamido]propion-N,N'-dimethyl-amidine hydrochloride;

3-[1-methyl-4-[1-methyl-4-[1-methyl-4-[3-methoxy-4-N-ethyl-N-( 2-chloroethyl)aminobenzene-1-carboxamido] pyrrole-2-carboxamido]pyrrole-2-carboxamido]pyrrole-2-carboxamido]propion-N,N'-dimethyl-amidine hydrochloride;

3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine hydrochloride;

3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propion-N,N'-dimethyl-amidine hydrobromide;

3-[1-methyl-4-[1-methyl-4-[1-methyl-4-[3-methyl-4-N-ethyl-N-(2-bromoethyl)aminobenzene-1-carboxamido] pyrrole-2-carboxamido]pyrrole-2-carboxamido]pyrrole-2-carboxamido]propion-N,N'-dimethyl-amidine hydrobromide; and 3-[1-methyl-4[1-methyl-4[1-methyl-4[4-N,N-bis(2-bromoethyl) aminobenzene-1-carboxamido]pyrrole-2-carboxamido]pyrrole-2-carboxamido]pyrrole-2-carboxamido]propion-N,N'-dimethyl-amidine.

EXAMPLE 5

3-[1-methyl-4-[1-methyl-4-[1-methyl-4-[4-N-ethyl-N-(2-chloroethyl)aminobenzene-1-carboxamido] pyrrole-2-carboxamido]pyrrole-2-carboxamido] pyrrole-2-carboxamido]propioncyanamidine Step I The Intermediate 3-[1-methyl-4-[1-methyl-4-[1-methyl-4-aminopyrrole-2-carboxamido]pyrrole-2-carboxamido]pyrrole-2-carboxamido] propioncyanamidine hydrochloride To a solution of 324 mg of cyanamide in 20 ml of DMF 186 mg of sodium hydride were added. The mixture was stirred at room temperature for 30 min. and then added to a solution of 1 g of distamycin A in 10 ml DMF. The solution was stirred at room temperature for two hours, then acetic acid was added until pH=7. The solvent was removed at reduced pressure and the crude residue purified by flash chromatography (methylene chloride/methanol: 9/1) to give 900 mg of 3-[1-methyl-4-[1-methyl-4-[1-methyl-4-formamidopyrrole-2-carboxamido]pyrrole-2-carboxamido] pyrrole-2-carboxamido]propioncyanamidine which was dissolved in 50 ml of methanol and added with 5 ml of 2 N hydrochloric acid.

The reaction mixture was stirred at room temperature for two days, the solvent was evaporated in vacuo and the solid residue suspended in 200 ml of ethyl acetate, yielding after filtration 600 mg of the intermediate.

FAB-MS: m/z 479 (65, [M+H]$^+$)

PMR (DMSO-d$_6$) δ: 10.11 (s, 3H), 9.97 (s, 1H), 9.80–9.60 (b.s., 2H), 8.50–8.00 (b.s., 3H), 7.40 (t, J=5.8 Hz, 1H), 7.25 (d, J=1.7 Hz, 1H), 7.19 (d, J=1.7 Hz, 1H), 7.08 (d, J=1.7 Hz, 1H), 7.06 (d, J=1.7 Hz, 1H), 6.94 (d, J=1.7 Hz, 1H), 6.88 (d, J=1.7 Hz, 1H), 3.81 (s, 3H), 3.79 (s, 3H), 3.75 (s, 3H), 3.41 (m, 2H), 2.70 (m, 2H).

Step II

The Title Compound

A solution of 180 mg of 4-N-ethyl-N-(2-chloroethyl) aminobenzoic acid (prepared as reported in Example 1, step II) and 1 ml of thionyl chloride in 20 ml of benzene was refluxed for two hours, then the solvent was evaporated in vacuo. The crude residue was dissolved in 10 ml dioxane and added in small portions to a solution of 110 mg of the intermediate obtained from step I and 40 mg of potassium bicarbonate in 20 ml of water.

The mixture was stirred at room temperature for one hour, the solvent was evaporated in vacuo and the crude residue purified by flash chromatography (methylene chloride/methanol: 8/2) to yield 90 mg of the title compound.

FAB-MS: m/z 688 (15, [M+H]$^+$)

PMR (DMSO-d$_6$ 45° C.) δ: 9.87 (s, 1H), 9.83 (s, 1H), 9.80 (s, 1H), 8.60–7.90 (b.s., 3H), 7.44 (m, 2H), 7.25 (d, J=1.6 Hz, 1H), 7.22 (d, J=1.6 Hz, 1H), 7.17 (d, J=1.6 Hz, 1H) 7.03 (d, J=1.6 Hz, 1H), 6.92 (d, J=1.6 Hz, 1H), 6.87 (d, J=1.6 Hz, 1H), 6.81 (m, 2H), 3.86 (s, 3H), 3.85 (s, 3H), 3.81 (s, 3H), 3.50–3.40 (m, 4H), 3.22 (m, 4 H), 2.6 (m, 2H), 1.61 (t, J=6.8 Hz, 3H).

By analogous procedure and using the suitable starting material the following products can be obtained:

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propioncyanamidine;

3-[1-methyl-4-[1-methyl-4-[1-methyl-4-[3-methyl-4-N-ethyl-N-(2-chloroethyl)aminobenzene-1-carboxamido] pyrrole-2-carboxamido]pyrrole-2-carboxamido]pyrrole-2-carboxamido]propioncyanamidine;

3-[1-methyl-4-[1-methyl-4-[1-methyl-4-[3,5-dimetyl-4-N-ethyl-N-(2-chloroethyl)aminobenzene-1-carboxamido] pyrrole-2-carboxamido]pyrrole-2-carboxamido]pyrrole-2-carboxamido]propioncyanamidine;

3-[1-methyl-4-[1-methyl-4-[1-methyl-4-[3-methoxy-4-N-ethyl-N-(2-chloroethyl)aminobenzene-1-carboxamido] pyrrole-2-carboxamido]pyrrole-2-carboxamido]pyrrole-2-carboxamido]propioncyanamidine;

3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido] propioncyanamidine;

3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propioncyanamidine; and 3-[1-methyl-4-[1-methyl-4-[1-methyl-4-[3-methyl-4-N-ethyl-N-(2-bromoethyl)aminobenzene-1-carboxamido] pyrrole-2-carboxamido]pyrrole-2-carboxamido]pyrrole-2-carboxamido]propioncyanamidine.

EXAMPLE 6

3-[1-methyl-4-[1-methyl-4-[1-methyl-4-[4-N-ethyl-N-(2-chloroethyl)aminobenzene-1-carboxamido] pyrrole-2-carboxamido]pyrrole-2-carboxamido] pyrrole-2-carboxamido]propionamidoxime A solution of 165 mg of 3-[1-methyl-4-[1-methyl-4-[1-methyl-4-[4-N-ethyl-N-(2-chloroethyl)aminobenzene-1- carboxamido]pyrrole-2-carboxamido]pyrrole-2-carboxamido]pyrrole-2-carboxamido]propionamidine hydrochloride (prepared as reported in Example 1) in 20 ml DMF was heated to 80° C. and treated with 0.48 ml of hydroxylamine 1M in DMF. After 30 min. additional 1 equivalent of hydroxylamine 1M in DMF was added. The solution was evaporated to dryness and the crude residue was purified by flash chromatography (methylene chloride/methanol: 9/1) to give 90 mg of the title compound as a white solid.

FAB-MS: m/z 679 (20, [M+H]$^+$)

PMR (DMSO-$d_6$) δ: 10.02 (s, 1H), 9.96 (s, 1H), 9.91 (s, 1H), 9.40 (b.s., 1H), 8.05 (t, J=5.6 Hz, 1H), 7.45 (m, 2H), 7.29 (d, J=1.7 Hz, 1H), 7.24 (d, J=1.7 Hz, 1H), 7.18 (d, J=1.7 Hz, 1H), 7.05 (d, J=1.7 Hz, 1H), 6.93 (d, J=1.7 Hz, 1H), 6.89 (d, J=1.7 Hz, 1H), 6.80 (m, 2H), 6.40–6.20 (b.s., 2H), 3.87 (s, 3H), 3.84 (s, 3H), 3.81 (s, 3H), 3.60–3.50 (m, 4H), 3.24 (m, 4 H), 2.62 (m, 2H), 1.15 (t, J=6.8 Hz, 3H).

By analogous procedure and using the suitable starting materials the following products can be obtained:

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propionamidoxime;

3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propionamidoxime;

3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propionamidoxime;

3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propionamidoxime;

3-[1-methyl-4-[1-methyl-4-[1-methyl-4-[3-trifluoromethyl-4-N-ethyl-N-(2-chloroethyl)aminobenzene-1-carboxamido]pyrrole-2 -carboxamido]pyrrole-2-carboxamido]pyrrole-2-carboxamido] propionamidoxime;

3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propionamidoxime;

3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propionamidoxime;

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propion-N-methyl-amidine hydrochloride;

3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]propion-N,N'-dimethyl-amidine hydrochloride; and 3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propioncyanamidine.

EXAMPLE 7

2-[1-methyl-4-[1-methyl-4-[1-methyl-4-[4-N-ethyl-N-(2-chloroethyl)aminobenzene-1-carboxamido] pyrrole-2-carboxamido]pyrrole-2-carboxamido] pyrrole-2-carboxamido]ethylguanidine hydrochloride

Step I

The Intermediate 2-aminoethylguanidine dihydrochloride

A solution of commercial N-BOC-ethylendiamine (1 g) in dry ethanol (100 ml) and 2-methyl-2-thiopseudourea hydroiodide (1.5 g) was refluxed for 8 hours. The solvent was removed at reduced pressure and the crude residue purified by flash chromatography (methylene chloride/methanol: 9/1) to yield 1.5 g of N-BOC-2-aminoethylguanidine hydroiodide as a yellow oil which was dissolved in methanolic hydrochloric acid solution 5N (20 ml) and stirred at room temperature for 3 hours. The white precipitate was collected, washed with dry ethanol, affording 700 mg of the intermediate.

FAB-MS: m/z 103 (20, [M+H]$^+$)

PMR (DMSO-$d_6$) δ: 8.38 (b.s., 3H), 7.97 (t, J=6 Hz, 1H), 7.51 (b.s., 4H), 3.45 (m, 2H), 2.92 (m, 2H).

Step II

The Intermediate 2-[1-methyl-4[1-methyl-4[1-methyl-4-aminopyrrole-2-carboxamido]pyrrole-2-carboxamido]pyrrole-2-carboxamido]ethylguanidine dihydrochloride A solution of 1-methyl-4-[1-methyl-4-[1-methyl-4-nitropyrrole-2-carboxamido]pyrrole-2-carboxamido] pyrrole-2-carboxylic acid (590 mg) (prepared as reported in Tetrahedron 34,2389–2391,1978) in 20 ml of DMF, 2-aminoethylguanidine dihydrochloride (500 mg), 1-hydroxybenzotriazole hydrate (350 mg), dicycloexylcarbodiimide (880 mg), and sodium bicarbonate (385 mg) was stirred at 70° C. for 4 hours. The solution obtained after filtration was evaporated in vacuo and the residue purified by flash chromatography (methylene chloride/methanol: 8/2) to yield 800 mg of 2-[1-methyl-4-[1-methyl-4-[1-methyl-4-nitropyrrole-2-carboxamido]pyrrole-2-carboxamido]pyrrole-2-carboxamido]ethylguanidine hydrochloride, which was dissolved in methanol (100 ml), added with 1N hydrochloric acid solution (2 ml) and reduced over Pd catalyst (10% on charcoal) in hydrogen atmosphere (50 psi) in a Parr apparatus. The solution obtained after filtration of the catalyst was evaporated in vacuo and the solid residue washed with dry ethanol to yield 750 mg of the intermediate as a brown powder.

FAB-MS: m/z 469 (15, [M+H]$^+$)

PMR (DMSO-$d_6$) δ: 10.38–10.11 (b.s., 4H), 9.98 (s, 1H), 8.28 (b.s., 1H), 8.19 (d, J=1.7 Hz, 1H), 7.73, (b.s., 1H), 7.63 (d, J=1.7 Hz, 1H), 7.60–7.00 (b.s., 4H), 7.28 (d, J=1.7 Hz, 1H), 7.20 (d, J=1.7 Hz, 1H), 7.1 (d, J=1.7 Hz, 1H), 6.92 (d, J=1.7 Hz, 1H), 3.93 (s, 3H), 3.90 (s, 3H), 3.82 (s, 3H), 3.28 (m, 4H).

By analogous procedure and using the suitable starting materials the following products can be obtained:

3-[1-methyl-4-[1-methyl-4-[1-methyl-4-aminopyrrole-2-carboxamido]pyrrole-2-carboxamido]pyrrole-2-carboxamido]propioncyanamidine hydrochloride;

3-[1-methyl-4-[1-methyl-4-[1-methyl-4-aminopyrrole-2-carboxamido]pyrrole-2-carboxamido]pyrrole-2-carboxamido]propion-N-methyl-amidine dihydrochloride;

3-[1-methyl-4-[1-methyl-4-[1-methyl-4-aminopyrrole-2-carboxamido]pyrrole-2-carboxamido]pyrrole-2-carboxamido]propion-N,N'-dimethyl-amidine dihydrochloride;

2-[1-methyl-4-[1-methyl-4-[1-methyl-4-aminopyrrole-2-carboxamido]pyrrole-2-carboxamido]pyrrole-2-carboxamido]ethyl-1-(2-imidazole) hydrochloride;

2-[1-methyl-4-[1-methyl-4-[1-methyl-4-aminopyrrole-2-carboxamido]pyrrole-2-carboxamido]pyrrole-2-carboxamido]ethyl-1-[2-(3,4,5,6-tetrahydropirimidine)] dihydrochloride;

2-[1-methyl-4[1-methyl-4[1-methyl-4-aminopyrrole-2-carboxamido]pyrrole-2-carboxamido]pyrrole-2-carboxamido]ethyl-1-(2-imidazoline) dihydrochloride;

3-[1-methyl-4[1-methyl-4[1-methyl-4-aminopyrrole-2-carboxamido]pyrrole-2-carboxamido]pyrrole-2-carboxamido]propionamide hydrochloride; and 3-[1-methyl-4[1-methyl-4[1-methyl-4-aminopyrrole-2-carboxamido]pyrrole-2-carboxamido]pyrrole-2-carboxamido]propionitrile hydrochloride.

Step III

The Title Compound

A solution of 600 mg of 4-N-ethyl-N-(2-chloroethyl)aminobenzoic acid (prepared as reported in example 1 step II) 3 ml of thionyl chloride in 60 ml of benzene was refluxed for two hours, then the solvent was evaporated in vacuo. The crude residue was dissolved in 50 ml dioxane and added in small portions to a solution of 250 mg of the intermediate and 125 mg of potassium bicarbonate in 10 ml of water. The mixture was stirred at room temperature for one hour, the solvent was evaporated under vacuo and the crude residue purified by flash chromatography (methylene chloride/methanol: 8/2) to yield 50 mg of the title compound as a yellow solid.

FAB-MS: m/z 678 (15, [M+H]$^+$); 210

PMR (DMSO-d$_6$) δ: 9.94 (s, 1H), 9.92 (s, 1H), 9.90 (s, 1H), 8.09 (b.s., 1H), 7.81 (m, 2H), 7.52 (b.s., 1H), 7.2 (b.s., 4H), 7.27 (d, J=1.7 Hz, 1H), 7.22(d, J=1.7 Hz, 1H), 7.17 (d, J=1.7 Hz, 1H), 7.07 (d, J=1.7 Hz, 1H), 7.05 (d, J=1.7 Hz, 1H), 6.95 (d, J=1.7 Hz, 1H), 6.75 (m, 2H), 3.85 (s, 3H), 3.84 (s, 3H), 3.81 (s, 3H), 3.72 (m, 4H), 3.47 (m, 2H), 3.30 (m, 4H), 1.10 (t, J=6.9 Hz, 3H).

By analogous procedure and using the suitable starting materials the following products can be obtained:

2-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]ethylguanidine hydrochloride;

2-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]ethylguanidine;

2-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]ethylguanidine hydrochloride;

2-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]ethylguanidine hydrochloride;

2-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]ethylguanidine hydrochloride;

2-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]ethylguanidine hydrochloride; and 2-[1-methyl-4-[1-methyl-4-[1-methyl-4-[3-methyl-4-N-ethyl-N-( 2-bromoethyl)aminobenzene-1-carboxamido]pyrrole-2-carboxamido]pyrrole-2-carboxamido]pyrrole-2-carboxamido]ethylguanidine hydrochloride;

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]propionamide;

3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N-methyl-amide;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionamide;

3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionamide; and 3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propion-N-methyl-amide.

EXAMPLE 8

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propionamidoxime Step I The Intermediate 3-[1-methyl-4-[1-methyl-4-[1-methyl-4-aminopyrrole-2-carboxamido]pyrrole-2-carboxamido]pyrrole-2-carboxamido]propionamidoxime hydrochloride 1.2 g of 3-[1-methyl-4-[1-methyl-4-[1-metyhyl-4-nitropyrrole-2-carboxamido]pyrrole-2-carboxamido]

pyrrole-2-carboxamido]propionitrile (prepared as reported in J.Med.Chem 22,1296–1301,1979) was suspended in dry ethanol and the solution saturated with dry hydrogen chloride. After 24 hours at room temperature, the solvent was evaporated under vacuo and the residue treated with two equivalents of solution of hydroxylamine in dry ethanol. After 24 hours at room temperature, the solvent was evaporated in vacuo and the residue purified by flash chromatography yielding 500 mg of 3-[1-methyl-4-[1-methyl-4-[1-methyl-4-nitropyrrole-2-carboxamido]pyrrole-2-carboxamido]pyrrole-2-carboxamido]propionamidoxime which was dissolved in a mixture of methanol-dioxane-10% hydrochloric acid (4:1:1) and reduced over Pd catalyst (10% on charcoal) in hydrogen atmosphere (50 psi) in a Parr apparatus.

The solution obtained after filtration of the catalyst was evaporated in vacuo, and the solid residue suspended in dry ethanol, and filtered to yield 500 mg of the intermediate.

FAB-MS: m/z 480 (20, [M+H]$^+$)

PMR (DMSO-$d_6$) $\delta$: 10.18 (b.s., 6H), 9.98 (s, 1H), 8.32 (t, J=5.7 Hz, 1H),7.25 (d, J=1.7 Hz, 1H), 7.20 (d, J=1.7 Hz, 1H), 7.16(d, J=1.7 Hz, 1H), 7.12 (d, J=1.7 Hz, 1H), 7.10 (d, J=1.7 Hz, 1H), 6.93 (d, J=1.7 Hz, 1H), 3.89 (s, 3H), 3.86 (s, 3H), 3.82 (b.s., 7H), 3.50 (m, 2H), 2.72 (m, 2H).

By analogous procedure and using the suitable starting materials the following products can be obtained:

3-[1-methyl-4-[1-methyl-4-[1-methyl-4-aminopyrrole-2-carboxamido]pyrrole-2-carboxamido]pyrrole-2-carboxamido]propioncyanamidine hydrochloride;

3-[1-methyl-4-[1-methyl-4-[1-methyl-4-aminopyrrole-2-carboxamido]pyrrole-2-carboxamido]pyrrole-2-carboxamido]propion-N-methyl-amidine dihydrochloride; and 2-[1-methyl-4-[1-methyl-4-[1-methyl-4-aminopyrrole-2-carboxamido]pyrrole-2-carboxamido]pyrrole-2-carboxamido]propion-N,N'-dimethyl-amidine dihydrochloride.

Step II

The Title Compound

A solution of 160 mg of 4-N-ethyl-N-(2-chloroethyl) aminobenzoic acid (prepared as reported in example 1 step II) and 106 mg of 1-hydroxybenzotriazole hydrate in 10 ml of DMF was stirred at 70° C. for four hours, cooled to room temperature and then added with 310 mg of the intermediate obtained from step I and 118 mg of potassium bicarbonate in 20 ml of water.

The mixture was stirred at room temperature for 2 hours, the solvent was evaporated in vacuo and the crude residue purified by flash chromatography (methylene chloride/methanol: 8/2) to yield 180 mg of the title compound as a yellow solid.

FAB-MS: m/z 679 (20, [M+H]$^+$)

PMR (DMSO-$d_6$) $\delta$: 10.02 (s, 1H), 9.96 (s, 1H), 9.91 (s, 1H), 9.40 (b.s., 1H), 8.05 (t, J=5.6 Hz, 1H), 7.45 (m, 2H), 7.29 (d, J=1.7 Hz, 1H), 7.24 (d, J=1.7 Hz, 1H), 7.18 (d, J=1.7 Hz, 1H), 7.05 (d, J=1.7 Hz, 1H), 6.93 (d, J=1.7 Hz, 1H), 6.89 (d, J=1.7 Hz, 1H), 6.80 (m, 2H), 6.40–6.20 (b.s., 2H), 3.87 (s, 3H), 3.84 (s, 3H), 3.81 (s, 3H), 3.60–3.50 (m, 4H), 3.24 (m, 4 H), 2.62 (m, 2H), 1.15 (t, J=6.8 Hz, 3H).

By analogous procedure and using the suitable starting materials the following products can be obtained:

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propionamidoxime;

3-[1-methyl-4-[1-methyl-4-[1-methyl-4-[3-methyl-4-N-ethyl-N-(2-chloroethyl)aminobenzene-1-carboxamido] pyrrole-2-carboxamido]pyrrole-2-carboxamido]pyrrole-2-carboxamido]propionamidoxime;

3-[1-methyl-4-[1-methyl-4-[1-methyl-4-[3,5-dimetyl-4-N-ethyl-N-(2-chloroethyl)aminobenzene-1-carboxamido] pyrrole-2-carboxamido]pyrrole-2-carboxamido]pyrrole-2-carboxamido]propionamidoxime;

3-[1-methyl-4-[1-methyl-4-[1-methyl-4-[3-methyl-4-N-ethyl-N-(2-chloroethyl)aminobenzene-1-carboxamido] pyrrole-2-carboxamido]pyrrole-2-carboxamido]pyrrole-2-carboxamido]propion-N-methyl-amidine hydrochloride;

3-[1-methyl-4-[1-methyl-4-[1-methyl-4-[3,5-dimetyl-4-N-ethyl-N-(2-chloroethyl)aminobenzene-1-carboxamido] pyrrole-2-carboxamido]pyrrole-2-carboxamido]pyrrole-2-carboxamido]propion-N-methyl-amidine hydrochloride;

3-[1-methyl-4-[1-methyl-4-[1-methyl-4-[3-methoxy-4-N-ethyl-N-(2-chloroethyl)aminobenzene-1-carboxamido] pyrrole-2-carboxamido]pyrrole-2-carboxamido]pyrrole-2-carboxamido]propion-N-methyl-amidine hydrochloride;

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine hydrochloride;

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propion-N,N'-dimethyl-amidine hydrochloride;

3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propion-N,N'-dimethyl-amidine hydrochloride;

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propioncyanamidine;

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propioncyanamidine;

3-[1-methyl-4-[1-methyl-4-[1-methyl-4-[3-methyl-4-N-ethyl-N-(2-chloroethyl)aminobenzene-1-carboxamido] pyrrole-2-carboxamido]pyrrole-2-carboxamido]pyrrole-2-carboxamido]propioncyanamidine;

2-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]ethylguanidine hydrochloride;

2-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]ethylguanidine hydrochloride;

2-[1-methyl-4-[1-methyl-4-[1-methyl-4-[3-methyl-4-N-ethyl-N-(2-chloroethyl)aminobenzene-1-carboxamido] pyrrole-2-carboxamido]pyrrole-2-carboxamido]pyrrole-2-carboxamido]ethylguanidine; and 2-[1-methyl-4-[1-methyl-4-[1-methyl-4-[3-methoxy-4-N-ethyl-N-(2-chloroethyl)aminobenzene-1-carboxamido] pyrrole-2-carboxamido]pyrrole-2-carboxamido]pyrrole-2-carboxamido]ethylguanidine hydrochloride.

EXAMPLE 9

2-[1-methyl-4-[1-methyl-4-[1-methyl-4-[4-N,N-bis (2-chloroethyl)aminobenzene-1-carboxamido] pyrrole-2-carboxamido]pyrrole-2-carboxamido] pyrrole-2-carboxamido]ethyl-1-(2-imidazoline) hydrochloride A solution of 300 mg of 3-[1-methyl-4-[1-methyl-4-[1-methyl-4-[4-N,N-bis-(2-chloroethyl)aminobenzene-1-carboxamido]pyrrole-2-carboxamido]pyrrole-2-carboxamido]pyrrole-2-carboxamido]propionamidine hydrochloride (prepared as reported in J.Med.Chem. 32,774–778, 1989) in 50 ml of acetonitrile and 20 ml of water was treated with ethylendiamine (0.2 ml). The resulting solution was kept at room temperature for 24 hours and the whole evaporated in vacuo. The residue was purified by flash chromatography (methylene chloride/methanol: 8/2) to give 80 mg of the title compound as a yellow solid.

FAB-MS: m/z 697, (15, [M+H]$^+$); 244, (18)

PMR(DMSO-$d_6$) δ: 10.00 (b.s., 2H), 10.03 (s, 1H), 9.95 (s, 1H), 9.92 (s, 1H), 8.29 (t, J=5.7Hz, 1H), 7.84 (m, 2H), 7.29 (d, J=1.8Hz, 1H), 7.23 (d, J=1.8Hz, 1H), 7.19(d, J=1.8Hz, 1H) 7.07 (d, J=1.8Hz, 1H), 7.06 (d, J=1.8Hz, 1H), 6.93 (d, J=1.8Hz, 1H), 6.82 (m, 2H), 3.90–3.60 (m, 12H), 3.85 (s, 3H), 3.83 (s, 3H), 3.80 (s, 3H), 3.48 (m, 2H), 2.68 (t, J=6.7Hz, 2H)

By analogous procedure and using the opportune starting materials the following compounds can be obtained:

2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)] hydrochloride FAB-MS: m/z 711, (20, [M+H]$^+$); 244, (40)

PMR(DMSO-$d_6$) δ: 10.15 (s, 1H), 9.90 (s, 2H), 8.25 (t, J=5.7Hz, 1H), 7.82 (m, 2H),7.27 (d, J=1.8Hz, 1H), 7.23 (d, J=1.8Hz, 1H), 7.20 (d, J=1.8Hz, 1H), 7.05(d, J=1.8Hz, 1H) 7.03 (d, J=1.8Hz, 1H), 6.92 (d, J=1.8Hz, 1H), 7.30–6.92 (m, 6H),6.84 (m, 2H), 3.84 (s, 3H), 3.82 (s, 3H), 3.81 (s, 3H), 3.73–3.63 (m,8H), 3.52–3.00 (m, 6H), 2.60 (t, J=6.7Hz, 2H), 1.75 (m, 2H);

2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazoline) hydrochloride;

2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)] hydrochloride;

2-[1-methyl-4-[1-methyl-4-[1-methyl-4-formamidopyrrole-2-carboxamido]pyrrole-2-carboxamido]pyrrole-2-carboxamido]ethyl-1-(2-imidazoline) hydrochloride;

2-[1-methyl-4-[1-methyl-4-[1-methyl-4-formamidopyrrole-2-carboxamido]pyrrole-2-carboxamido]pyrrole-2-carboxamido]ethyl-1-[2-(3,4,5,6-tetrahydropirimidine)] hydrochloride.

EXAMPLE 10

2-[1-methyl-4[1-methyl-4[1-methyl-4[4-N,N-bis(2-chloroethyl) aminobenzene-1-carboxamido]pyrrole-2-carboxamido]pyrrole-2 -carboxamido]pyrrole-2-carboxamido]ethyl-1-(2-imidazole)

A solution of 200 mg of 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionamidine hydrochloride (prepared as reported in J. Med. Chem. 32, 774–778, 1989) in 10 ml of DMB was treated with 90 μl of aminoacetaldehyde dimethylacetale and heated at 70° C. for 4 hours. The solvent was removed under reduced pressure and the crude product was purified by flash chromatography (methylene chloride/methanol: 9/1) to give 40 mg of the title compound as a yellow solid.

FAB-MS: m/z 721, (8, [M+H]$^+$); 244, (100)

PMR(DMSO-$d_6$) δ: 10.01 (s, 1H), 9.94 (s, 1H), 9.90 (s, 1H), 8.12 (t, J=5.8Hz, 1H), 7.84 (m, 2H), 7.30 (d, J=1.8Hz, 1H), 7.24 (d, J=1.8Hz, 1H), 7.20 (d, J=1.8Hz, 1H) 7.06 (d, J=1.8Hz, 1H), 7.04 (d, J=1.8Hz, 1H), 6.83 (d, J=1.8Hz, 1H), 6.87 (s, 2H), 6.82 (m, 2H), 3.42 (m, 2H), 3.85 (s, 3H), 3.83(s, 3H), 3.80 (s, 3H), 3.48 (m, 3H), 2.81 (m, 2H)

By analogous procedure and using the opportune starting materials the following products can be obtained:

2-[1-methyl-4[1-methyl-4[1-methyl-4[3-methyl-4-N,N-bis (2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3,5-dimethyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4-formamidopyrrole-2-carboxamido]pyrrole-2-carboxamido]pyrrole-2-carboxamido]ethyl-1-(2-imidazole).

EXAMPLE 11

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propion-N-methyl-amidine hydrochloride A solution of 200 mg of 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionamidine hydrochloride (prepared as reported in J. Med. Chem. 32, 774–778, 1989) in 5 ml DMF was treated with 0.023 ml of methylamine hydrochloride 80%. After 4 h additional 0.5 equivalent of methylamine hydrochloride 80% was added. The solution was evaporated to dryness and the crude residue was purified by flash chromatography (methylene chloride/methanol: 9/1) to give 100 mg of the title compound as a white solid.

FAB-MS: m/z 710, (20, [M+H]$^+$)

PMR (DMSO-$d_6$) δ: 10.07 (S, 1H), 9.98 (s, 1H), 9.95 (s, 1H), 9.65–9.45 (b.s., 1H), 9.25–9.05 (b.s., 1H), 8.70–8.50 (b.s., 1H), 8.26 (t, J=5.8Hz, 1H), 7.86 (m, 2H), 7.31 (d, J=1.7Hz, 1H), 7.25 (d, J=1.7Hz, 1H), 7.20(d, J=1.7Hz, 1H) 7.10 (d, J=1.7Hz, 1H), 7.07 (d, J=1.7Hz, 1H), 6.93 (d, J=1.7Hz, 1H), 6.82 (m, 2H), 3.86 (s, 3H), 3.84 (s, 3H), 3.80 (s, 3H), 3.75–3.55 (m, 8H), 3.45 (m, 2H), 2.79 (s, 3H), 2.55 (m, 2H)

By analogous procedure and using the opportune starting material the following product can be obtained:

3-[1-methyl-4[1-methyl-4[1-methyl-4[3-methyl-4-N,N-bis (2-chloroethyl)aminobenzene-1-carboxamido]pyrrole-2- carboxamido]pyrrole-2-carboxamido]pyrrole-2-carboxamido]propion-N-methyl-amidine hydrochloride.

EXAMPLE 12

3[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propion-N,N'-dimethylamidine hydrochloride A solution of 200 mg of 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionamidine hydrochloride (prepared as reported in J. Med. Chem. 32, 774–778, 1989) in 5 ml DMF was heated at 70° C. and treated with 0.115 ml of methylamine hydrochloride 80%. After 4 h additional 5 equivalent of methylamine hydrochloride 80% was added. The solution was evaporated to dryness and the crude residue was purified by flash chromatography (methylene chloride/methanol: 9/1) to give 120 mg of the title compound as a white solid.

FAB-MS: m/z, 724 (25, [M+H]$^+$)

PMR (DMSO-d$_6$) δ: 10.07 (s, 1H), 9.98 (s, 1H), 9.96 (s, 1H), 9.60–9.40 (b.s., 1H), 8.85–8.65 (b.s., 1H), 8.34 (t, J=5.2Hz, 1H), 7.85 (m, 2H), 7.30 (d, J=1.5Hz, 1H), 7.24 (d, J=1.5Hz, 1H), 7.20(d, J=1.5Hz, 1H) 7.07 (m, 2H), 6.93 (d, J=1.5Hz, 1H), 6.82 (m, 2H), 3.86 (s, 3H), 3.84 (s, 3H), 3.80 (s, 3H), 3.75–3.55 (m, 8H), 3.40 (m, 2H), 3.00 (s, 3H), 2.78 (s, 3H), 2.60 (m, 2H)

By analogous procedure and using the opportune starting material the following product can be obtained:
3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propion-N,N'-dimethylamidine hydrochloride.

EXAMPLE 13

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionamidoxime A solution of 500 mg of 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionamidine hydrochloride (prepared as reported in J. Med. Chem. 32, 774–778, 1989) in 20 ml DMF was heated at 60° C. and treated with 0.68 ml of hydroxylamine 1M in DMF obtained from hydroxylamine hydrochloride (70 mg), 0.139 ml triethylamine and 1 ml DMF with 10% water. After 30' additional 1 equivalent of hydroxylamine 1M in DMF was added. The solution was evaporated to dryness and the crude residue was purified by flash chromatography (methylene chloride/methanol: 85/15) to give 400 mg of the title compound as a white solid.

FAB-MS: m/z 713, (70, [M+H]$^+$); 244, (40)

U.V. (MeOH) λ$_{max}$ 312.85, ε=56445

PMR (DMSO-d$_6$) δ: 9.98 (s, 1H), 9.92 (s, 1H), 9.86 (s, 1H), 8.82 (s, 1H), 7.87 (t, J=5.7Hz, 1H), 7.83 (m, 2H), 7.28 (d, J=1.7Hz, 1H), 7.23 (d, J=1.7Hz, 1H), 7.17(d, J=1.7Hz, 1H) 7.06 (d, J=1.7Hz, 1H), 7.04 (d, J=1.7Hz, 1H), 6.83 (d, J=1.7Hz, 1H), 6.82 (m, 2H), 5.40 (b.s., 2H), 3.90–3.70 (m, 8H), 3.85 (s, 3H), 3.83(s, 3H), 3.79 (s, 3H), 3.32 (m, 2H), 2.20 (m, 2H)

By analogous procedure and using the opportune starting material the following product can be obtained:
3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionamidoxime;
3-[1-methyl-4[1-methyl-4[1-methyl-4[4-N,N-bis(2-bromoethyl) aminobenzene-1-carboxamido]pyrrole-2-carboxamido]pyrrole-2-carboxamido]pyrrole-2-carboxamido]propionamidoxime.

EXAMPLE 14

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propioncyanamidine To a solution of 50 mg of cyanamide in 5 ml of DMF were added 30 mg of sodium hydride. The mixture was stirred at room temperature for 15' and then added to a solution of 200 mg of 3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionamidine hydrochloride (prepared as reported in J. Med. Chem. 32, 774–778, 1989) in 5 ml DMF. The solution was stirred at room temperature for 30', then acetic acid was added until pH=7. The solvent removed under reduced pressure and the crude residue was purified by flash chromatography (methylene chloride/methanol: 9/1) to give 90 mg of the title compound as a white solid.

FAB-MS: m/z 722, (10, [M+H]$^+$); 366, (10); 244, (80)

PMR(DMSO-d$_6$, 75° C.) δ: 9.76 (s, 1H), 9.68 (s, 1H), 9.65 (s, 1H), 8.10 (b.s., 1H), 8.00 (b.s., 1H), 7.84(m, 3H), 7.24 (d, J=1.8Hz, 1H), 7.19 (d, J=1.8Hz, 1H), 7.15(d, J=1.8Hz, 1H), 7.05 (d, J=1.8Hz, 1H), 7.03 (d, J=1.8Hz, 1H), 6.87 (d, J=1.8Hz, 1H), 6.83 (m, 2H), 3.90–3.70 (m, 8H), 3.87 (s, 3H), 3.86(s, 3H), 3.82 (s, 3H), 3.48 (m, 2H), 2.61 (m, 2H)

By analogous procedure and using the opportune starting materials the following products can be obtained:
3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propioncyanamidine;
3-[1-methyl-4[1-methyl-4[1-methyl-4[3,5-dimethyl-4-N,N-bis(2-chloroethyl)aminobenzene-1-carboxamido]pyrrole-2-carboxamido]pyrrole-2-carboxamido]pyrrole-2-carboxamido]propioncyanamidine;
3-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]propioncyanamidine;
3-[1-methyl-4[1-methyl-4[1-methyl-4-formamidopyrrole-2-carboxamido]pyrrole-2-carboxamido]pyrrole-2-carboxamido]propioncyanamidine.

EXAMPLE 15

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionamidrazone A solution of 250 mg of 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionamidine hydrochloride (prepared as reported in J. Med. Chem. 32, 774–778, 1989) in 8 ml DMF and 0.04 ml of hydrazine hydrate was stirred for 15' at 25° C. then 2N hydrochloric acid was added until pH=5, the solvent was evaporated in vacuo and the residue was purified by flash chromatography (methylene chloride/methanol: 9/1) to give 100 mg of the title compound as a yellow solid.

FAB-MS: m/z 712, [18, (M+H)$^+$]

PMR(DMSO-d$_6$) δ: 10.05 (s, 1H), 9.93 (s, 1H), 9.90 (s, 1H), 8.70 (b.s., 2H), 8.19 (t, J=5.70Hz, 1H), 7.83 (m, 2H), 7.27 (d, J=1.8Hz, 1H), 7.21 (d, J=1.8Hz, 1H), 7.16 (d, J=1.8Hz, 1H), 7.06 (d, J=1.8Hz, 1H), 7.03 (d, J=1.8Hz, 1H), 6.91 (d, J=1.8Hz, 1H), 6.78 (m, 2H), 5.00 (b.s., 2H), 3.90–3.60 (m, 8H), 3.81 (s, 3H), 3.79(s, 3H), 3.76 (s, 3H), 3.44 (m, 2H), 2.57 (t, J=6.5Hz, 2H)

By analogous procedure and using the opportune starting material the following product can be obtained:

3-[1-methyl-4[1-methyl-4[1-methyl-4[3-methyl-4-N,N-bis (2-chloroethyl)aminobenzene-1-carboxamido]pyrrole-2-carboxamido]pyrrole-2-carboxamido]pyrrole-2-carboxamido]propionamidrazone.

EXAMPLE 16

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionitrile To a solution of 1.30 g of 3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionamidine hydrochloride (prepared as reported in J. Med. Chem. 32, 774–778, 1989) in 20 ml DMF were added 535 mg of potassium carbonate and 385 mg of succinic anhydride. The mixture was heated at 60° C. for 4 hours. The solvent evaporated under vacuum and the crude residue purified by flash chromatography (methylene chloride/methanol: 8/2) to yield 600 mg of the title compound as a yellow powder.

FAB-MS: m/z 680, (8, [M+H]$^+$); 488, (10); 366, (15); 244, (100)

PMR(DMSO-d$_6$) δ: 10.01 (s, 1H), 9.96 (s, 1H), 9.94 (s, 1H), 8.34 (t, J=6.0Hz, 1H), 7.84 (m, 2H), 7.30 (d, J=1.8Hz, 1H), 7.25 (d, J=1.8Hz, 1H), 7.22 (d, J=1.8Hz, 1H), 7.07 (d, J=1.8Hz, 1H), 7.05 (d, J=1.8Hz, 1H), 6.94 (d, J=1.8Hz, 1H), 6.83 (m, 2H), 3.90–3.60 (m, 8H), 3.86 (s, 3H), 3.84(s, 3H), 3.80 (s, 3H), 3.40 (m, 2H), 2.72 (t, J=6.4Hz, 2H)

By analogous procedure and using the opportune starting materials the following products can be obtained:

3-[1-methyl-4[1-methyl-4[1-methyl-4[3-methyl-4-N,N-bis (2-chloroethyl)aminobenzene-1-carboxamido]pyrrole-2-carboxamido]pyrrole-2-carboxamido]pyrrole-2-carboxamido]propionitrile;

3-[1-methyl-4[1-methyl-4[1-methyl-4-formamidopyrrole-2-carboxamido]pyrrole-2-carboxamido]pyrrole-2-carboxamido]propionitrile.

EXAMPLE 17

2-[1-methyl-4[1-methyl-4[1-methyl-4[4-N,N-bis(2-chloroethyl) aminobenzene-1-carboxamido]pyrrole-2-carboxamido]pyrrole-2 -carboxamido]pyrrole-2-carboxamido]ethylguanidine hydrochloride A solution of 4-[N,N-bis(2-chloroethyl)amino]benzoyl chloride (590 mg) (prepared as reported in J. Med. Chem. 32, 774–778, 1989) in 20 ml of dioxane was added slowly to a solution of the intermediate obtained in Example 7, step II, above (500 mg) in 20 ml of water containing sodium bicarbonate (237 mg). The mixture was stirred at room temperature for 3 hours, the aqueous solution was evaporated in vacuo to dryness and the solid residue purified by flash chromatography (methylene chloride/methanol: 8/2) to yield 450 mg of the title compound as a yellow powder.

FAB-MS: m/z 712, (20, [M+H]$^+$); 244, (100)

U.V. (EtOH 95%) $\lambda_{max}$=312.8, ε=54227

PMR(DMSO-d$_6$) δ: 10.02 (s, 1H), 9.93 (s, 1H), 9.91 (s, 1H), 8.85 (m, 2H), 8.12 (b.s., 1H), 7.65 (b.s.,1H), 7.20 (b.s., 4H), 7.29 (d, J=1.8Hz, 1H), 7.23 (d, J=1.8Hz, 1H), 7.19 (d, J=1.8Hz, 1H), 7.08 (d, J=1.8Hz, 1H), 7.06 (d, J=1.8Hz, 1H), 6.94 (d, J=1.8Hz, 1H), 6.82 (m, 2H), 3.90–3.70 (m, 8H), 3.85 (s, 3H), 3.84(s, 3H), 3.81 (s, 3H), 3.40–3.10 (m, 4H)

By analogous procedure and using the opportune starting materials the following products can be obtained:

2-[1-methyl-4[1-methyl-4[1-methyl-4[3-methyl-4-N,N-bis (2-chloroethyl)aminobenzene-1-carboxamido]pyrrole-2-carboxamido]pyrrole-2-carboxamido]pyrrole-2-carboxamido]ethylguanidine hydrochloride;

2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3,6-dimethyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)] hydrochloride;

2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)] hydrochloride;

2-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]ethyl-1-(2-imidazoline) hydrochloride;

2-[1-methyl-4[1-methyl-4[1-methyl-4[3-methyl-4-N,N-bis (2-chloroethyl)aminobenzene-1-carboxamido]pyrrole-2-carboxamido]pyrrole-2-carboxamido]pyrrole-2-carboxamido]ethyl-1-(2 -imidazoline) hydrochloride;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[3-methyl-4-N,N-bis (2-chloroethyl)aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionitrile;

3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionitrile;

3-[1-methyl-4[1-methyl-4[1-methyl-4[4-N,N-bis(2-bromoethyl) aminobenzene-1-carboxamido]pyrrole-2-carboxamido]pyrrole-2-carboxamido]pyrrole-2-carboxamido]propionitrile.

EXAMPLE 18

2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-(2-imidazoline) hydrochloride

Step I

The Intermediate 2-[1-methyl-4-[1-methyl-4-[1-methyl-4-formamidopyrrole-2-carboxamido]pyrrole-2-carboxamido]pyrrole-2-carboxamido]ethyl-1-(2-imidazoline)

A solution of 3 g of distamycin A in 40 ml of methanol was treated with ethylendiamine (1 ml). The resulting solution was kept at room temperature for 10 hours and the whole evaporated in vacuo. The residue was purified by flash chromatography (methylene chloride/methanol: 9/1) to give 1.1 g of intermediate.

FAB-MS: m/z 508, (50, [M+H]$^+$)

PMR(DMSO-$d_6$) δ: 10.12 (s, 1H), 9.91 (s, 2H), 8.27 (t, J=5.8 Hz, 1H), 8.11 (s, 1H), 7.22, (m, 3H), 7.1 (d, J=1.7 Hz, 1H), 6.92 (m, 2 H), 3.73 (s, 3H), 3.72 (s, 3H), 3.68 (s, 3H), 3.40 (t, J=6.4 Hz 2H), 2.62 (t, J=6.4 Hz, 2H)

By analogous procedure and using the opportune starting material the following product can be obtained:

2-[1-methyl-4-[1-methyl-4-[1-methyl-4-formamidopyrrole-2-carboxamido]pyrrole-2-carboxamido]pyrrole-2-carboxamido]ethyl-1-(2-imidazole)

PMR(DMSO-$d_6$) δ: 10.1 (s, 1H), 9.91 (s, 2H), 8.01 (s, 1H), 8.3 (t, J=5.8 Hz, 1H), 8.25 (s, 1H), 7.48, (s, 2H), 7.22 (d, J=1.7 Hz, 1H), 7.19 (d, J=1.7 Hz, 1H), 7.05 (d, J=1.7 Hz, 1H), 6.90 (m, 2H), 6.82 (d, J=1.7 Hz, 1H), 3.87 (s, 3H), 3.81 (s, 3H), 3.75 (s, 3H), 3.21 (m, 2H), 2.82 (t, J=6.4 Hz, 2H).

Step II

The Title Compound

A solution of 1.1 g of intermediate obtained from step I in 1M aqueous oxalic acid solution (80 ml) was stirred at 80° C. for 8 hours, the solution was neutralized with sodiun bicarbonate and diluted with ethanol. The solution obtained after filtration of the solid was acidified with 2N hydrochloric acid solution and then evaporated to dryness. The residue was purified by flash chromatography (methylene chloride/methanol: 6/4) to give 700 mg of 2-[1-methyl-4-[1-methyl-4-[1-methyl-4-aminopyrrole-2-carboxamido]pyrrole-2-carboxamido]pyrrole-2-carboxamido]ethyl-1-(2-imidazole) as a brown solid which was dissolved in a mixture of dioxane/water (50/10) containing sodium bicarbonate (500 mg). To the solution was added slowly a solution of 4[N,N-bis(2-chloroethyl)amino]benzoyl chloride (1.15 g) (prepared as reported in J. Med. Chem. 32, 774–778, 1989). The mixture was stirred at room temperature for 1 hour, the aqueous solution was acidified with 2 N hydrochloric acid solution until pH=3, The solvent evaporated in vacuo to dryness and the solid residue purified by flash chromatography (methylene chloride/methanol: 8/2) to yield 750 mg of the title compound as a yellow powder.

FAB-MS: m/z 697, (15,[M+H]$^+$); 244, (18)

PMR(DMSO-$d_6$) δ: 10.00 (b.s., 2H), 10.03 (s, 1H), 9.95 (s, 1H), 9.92 (s, 1H), 8.29 (t, J=5.7Hz, 1H), 7.84 (m, 2H), 7.29 (d, J=1.8Hz, 1H), 7.23 (d, J=1.8Hz, 1H), 7.19(d, J=1.8Hz, 1H) 7.07 (d, J=1.8Hz, 1H), 7.06 (d, J=1.8Hz, 1H), 6.93 (d, J=1.8Hz, 1H), 6.82 (m, 2H), 3.90–3.60 (m, 12H), 3.85 (s, 3H), 3.83 (s, 3H), 3.80 (s, 3H), 3.48 (m, 2H), 2.68 (t, J=6.7Hz, 2H)

By analogous procedure and using the opportune starting materials the following products can be obtained:

2-[1-methyl-4-[1-methyl-4-[1-methyl-4-[3-methyl-4-N,N-bis(2 -chloroethyl)aminobenzene-1-carboxamido]pyrrole-2-carboxamido]pyrrole-2-carboxamido]pyrrole-2-carboxamido]ethyl-1-(2-imidazoline) hydrochloride;

2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)] hydrochloride;

2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)] hydrochloride;

2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3,6-dimethyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[3,5-dimethyl-4-N,N-bis(2-chloroethyl)aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionitrile;

3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionitrile.

EXAMPLE 19

2-[1-methyl-4-[1-methyl-4-[1-methyl-4-[4-N,N-bis (2-chloroethyl)aminobenzene-1-carboxamido] pyrrole-2-carboxamido]pyrrole-2-carboxamido] pyrrole-2-carboxamido]ethyl-1-(2-imidazoline) hydrochloride

Step I

The Intermediate 3-[1-methyl-4-[1-methyl-4-[1-metyhyl-4-aminopyrrole-2-carboxamido]pyrrole-2-carboxamido]pyrrole-2-carboxamido]ethyl-1-(2-imidazoline) dihydrochloride 300 mg of 3-[1-methyl-4-[1-methyl-4-[1-metyhyl-4-nitropyrrole-2-carboxamido]pyrrole-2-carboxamido] pyrrole-2-carboxamido]propionitrile (prepared as reported in J.Med.Chem 22,1296–1301,1979) was suspended in anydrous ethanol and the solution satured with dry hydrochloric acid gas. After 24 hours at room temperature, the solvent was evaporated in vacuo and the residue treated with 47 $\mu$l of ethylendiamine in dry ethanol. After 24 hours at room temperature, the solvent was evaporated in vacuo and the residue purified by flash chromatography yelding 100 mg of 3-[1-methyl-4-[1-methyl-4-[1-metyhyl-4-nitropyrrole-2-carboxamido]pyrrole-2-carboxamido]pyrrole-2-carboxamido]ethyl-1-(2-imidazoline) hydrochloride which was dissolved in a mixture of methanol-dioxane-10% hydrochloric acid (4:1:1) and reduced over Pd catalyst (10% on chorcoal) under hydrogen pressure (50 psi) in a Parr apparatus.

The solution obtained after filtration of the catalyst was evaporated in vacuo, the solid residue suspended in dry ethanol, filtrated to yield 100 mg of intermediate.

FAB-MS: m/z 480, (20, [M+H]$^+$).

PMR(DMSO-d$_6$) $\delta$: 10.18 (b.s., 6H), 9.98 (s, 1H), 8.32 (t, J=5.7Hz, 1H),7.25 (d, J=1.7Hz, 1H), 7.20 (d, J=1.7Hz, 1H), 7.16(d, J=1.7Hz, 1H), 7.12 (d, J=1.7Hz, 1H), 7.10 (d, J=1.7Hz, 1H), 6.93 (d, J=1.7Hz, 1H), 3.89 (s, 3H), 3.86 (s, 3H), 3.82 (b.s., 7H), 3.50 (m, 2H), 2.72 (m, 3H)

By analogous procedure and using the opportune starting materials the following product can be obtained:

2-[1-methyl-4-[1-methyl-4-[1-methyl-4-aminopyrrole-2-carboxamido]pyrrole-2-carboxamido]pyrrole-2-carboxamido]ethyl-1-[2-(3,4,5,6-tetrahydropirimidine)] dihydrochloride;

2-[1-methyl-4-[1-methyl-4-[1-methyl-4-aminopyrrole-2-carboxamido]pyrrole-2-carboxamido]pyrrole-2-carboxamido]ethyl-1-(2-imidazole) hydrochloride;

3-[1-methyl-4[1-methyl-4[1-methyl-4-aminopyrrole-2-carboxamido]pyrrole-2-carboxamido]pyrrole-2-carboxamido]propioncyanamidine hydrochloride;

3-[1-methyl-4[1-methyl-4[1-methyl-4-aminopyrrole-2-carboxamido]pyrrole-2-carboxamido]pyrrole-2-carboxamido]ethyl-N-methyl-amidine dihydrochloride;

2[1-methyl-4[1-methyl-4[1-methyl-4-aminopyrrole-2-carboxamido]pyrrole-2-carboxamido]pyrrole-2-carboxamido]ethyl-N,N'-dimethyl-amidine dihydrochloride;

3-[1-methyl-4[1-methyl-4[1-methyl-4aminopyrrole-2-carboxamido]pyrrole-2-carboxamido]pyrrole-2-carboxamido]propionamidoxime hydrochloride;

3-[1-methyl-4[1-methyl-4[1-methyl-4-aminoe-2-carboxamido]pyrrole-2-carboxamido]pyrrole-2-carboxamido]propioncyanamidine hydrochloride;

3-[1-methyl-4[1-methyl-4[1-methyl-4-aminopyrrole-2-carboxamido]pyrrole-2-carboxamido] propioncyanamidine hydrochloride;

3-[1-methyl-4[1-methyl-4[1-methyl-4-aminoe-2-carboxamido]pyrrole-2-carboxamido]pyrrole-2-carboxamido]propionamidrazone hydrrochloride.

Step II

The Title Compound

A solution of 4-[N,N-bis(2-chloroethyl)amino]benzoyl chloride (175 mg) (prepared as reported in J. Med. Chem. 32, 774–778, 1989) in 20 ml of dioxane was added slowly to a solution of the intermediate obtained from step II (100 mg) in 20 ml of water containing sodium bicarbonate (53 mg). The mixture was stirred at room temperature for 3 hours, the aqueous solution was evaporated in vacuo to dryness and the solid residue purified by flash chromatography (methylene chloride/methanol: 8/2) to yield 100 mg of the title compound as a yellow solid.

FAB-MS: m/z 697, (15, [M+H]$^+$); 244, (18)

PMR(DMSO-d$_6$) $\delta$: 10.00 (b.s., 2H), 10.03 (s, 1H), 9.95 (s, 1H), 9.92 (s, 1H), 8.29 (t, J=5.7Hz, 1H), 7.84 (m, 2H), 7.29 (d, J=1.8Hz, 1H), 7.23 (d, J=1.8Hz, 1H), 7.19(d, J=1.8Hz, 1H) 7.07 (d, J=1.8Hz, 1H), 7.06 (d, J=1.8Hz, 1H), 6.93 (d, J=1.8Hz, 1H), 6.82 (m, 2H), 3.90–3.60 (m, 12H), 3.85 (s, 3H), 3.83 (s, 3H), 3.80 (s, 3H), 3.48 (m, 2H), 2.68 (t, J=6.7Hz, 2H)

By analogous procedure and using the opportune starting materials the following product can be obtained:

2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazoline) hydrochloride;

2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)] hydrochloride;

2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)] hydrochloride;

2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3,5-dimethyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[3,6-dimethyl-4-N,N-bis(2-chloroethyl)aminobenzene-1-carboxamido]pyrrole- 2-carboxamido]pyrrole-2-carboxamido]pyrrole-2-carboxamido]propioncyanamidine;

3-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]propioncyanamidine.

EXAMPLE 20

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionamide

Step I

The Intermediate 3-[1-methyl-4[1-methyl-4[1-methyl-4-aminopyrrole-2-carboxamido]pyrrole-2-carboxamido]pyrrole-2-carboxamido]propionamide hydrochloride To a solution of 1 g of distamycin A in 50 ml of acetonitrile and 50 ml of water, 10 ml of NaOH 1N, were added and the solution was heated at 60° C. for 4 hours. The solvent was evaporated to dryness and the crude residue was purified by flash chromatography (methylene chloride/methanol: 9/1) affording 800 mg of 3-[1-methyl-4[1-methyl-4[1-methyl-4-formamidopyrrole-2-carboxamido]pyrrole-2-carboxamido]pyrrole-2-carboxamido]propionamide which was dissolved in 20 ml of methanol and added of 5 ml of HCl 2N. The reaction was stirred at room temperature for 2 days, the solvent was evaporated in vacuo and the solid residue suspended in 50 ml of ethyl acetate, yielding after filtration 600 mg of the intermediate as a light brown solid.

By analogous procedure and using the opportune starting material the following product can be obtained:
3-[1-methyl-4[1-methyl-4[1-methyl-4-aminopyrrole-2-carboxamido]pyrrole-2-carboxamido]pyrrole-2-carboxamido]propion-N-methylamide hydrochloride.

Step II

The Title Compound

A solution of 260 mg of 4[N,N-bis(2-chloroethyl)amino]benzoylchloride (prepared as reported in J. Med. Chem., 32, 774–778 (1989)) in 25 ml of dioxane, was added to a solution of the intermediate obtained from step II (420 mg) in 25 ml of acetonitrile and 25 ml dioxane and 0.27 ml of triethylamine. The solution was stirred for 1 hour at room temperature, then evaporated in vacuo and the crude residue was purified by flash chromatography (methylene chloride/methanol: 8/2) to yield 220 mg of the title compound as a white solid.

FAB-MS: m/z 698, (36, [M+H]$^+$)

PMR (DMSO-d$_6$) δ: 10.07 (s, 1H), 9.94 (s, 1H), 9.90 (s, 1H), 7.96 (t, J=5.9 Hz, 1H), 7.85 (m, 2H), 7.34 (b.s., 2H), 7.26 (d, J=1.8 Hz, 1H), 7.18 (d, J=1.8 Hz, 1H), 7.31 (d, J=1.8 Hz, 1H).

By analogous procedure and using the opportune starting materials the following products can be obtained:
3-[1-methyl-4-[1-methyl-4-[1-methyl-4-[4-N-ethyl-N-(2-chloroethyl)aminobenzene-1-carboxamido]pyrrole-2-carboxamido]yrrole-2-carboxamido]pyrrole-2-carboxamido]propionamide;

3-[1-methyl-4-[1-methyl-4-[1-methyl-4-[4-N-propyl-N-(2-chloroethyl)aminobenzene-1-carboxamido]pyrrole-2-carboxamido]yrrole-2-carboxamido]pyrrole-2-carboxamido]propionamide;

3-[1-methyl-4-[1-methyl-4-[1-methyl-4-[3-methyl-4-N-ethyl-N-(2-chloroethyl)aminobenzene-1-carboxamido]pyrrole-2-carboxamido]yrrole-2-carboxamido]pyrrole-2-carboxamido]propionamide;

3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N-methyl-amide;

3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionamide;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propion-N-methyl-amide.

EXAMPLE 21

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propion-N-methyl-amide To a solution of 500 mg of 3[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propion-N,N'-dimethylamidine hydrochloride, prepared as reported in Example 12 above, dissolved in 70 ml of acetonitrile and 30 ml of water, 2.4 ml NaOH 1 N were added. The solution was refluxed for 2 hours, then evaporated to dryness. The crude residue was purified by flash chromatography (methylene chloride/methanol 9:1), affording 250 mg of the title compound as a white powder.

FAB-MS: m/z 712, (10, [M+H]$^+$)

PMR (DMSO-d$_6$) δ: 10.04 (s, 1H), 10.00 (s, 1H), 9.95 (s, 1H), 8.02 (t, J=5.7 Hz, 1H), 7.87 (m, 2H), 7.80 (q, J=5.4 Hz, 1H), 7.31 (d, J=1.8 Hz, 1H), 7.25 (d, J=1.8 Hz, 1H), 7.18 (d, J=1.8 Hz, 1H), 7.14 (d, J=1.8 Hz, 1H), 7.12 (d, J=1.8 Hz, 1H), 6.82 (m, 2H), 6.80 (d, J=1.8 Hz, 1H), 3.88 (s, 3H), 3.85 (s, 3H), 3.83 (s, 3H), 3.78 (m, 8H), 3.41 (m, 2H), 2.60 (d, J=5.4 Hz, 3H), 2.25 (m, 2H)

By analogous procedure and using the opportune starting materials the following products can be obtained:
3-[1-methyl-4-[1-methyl-4-[1-methyl-4-[4-N-ethyl-N-(2-chloroethyl)aminobenzene-1-carboxamido]pyrrole-2- carboxamido]pyrrole-2-carboxamido]pyrrole-2-carboxamido]propionamide;

3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N-methyl-amide;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionamide.

EXAMPLE 22

Tablets each weighing 0.250 g and containing 50 mg of the active substance can be manufactured as follows:

| Composition for 10,000 tablets | |
|---|---|
| 3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido] propionamidine hydrochloride | 500 g |
| Lactose | 1,400 g |
| Corn starch | 500 g |
| Talc powder | 80 g |
| Magnesium stearate | 20 g |

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propionamidine hydrochloride, lactose and half of the corn starch were mixed; the mixture was then forced through a sieve of 0.5 mm mesh size.

Corn starch (10 g) was suspended in warm water (90 ml) and the resulting paste was used to granulate the powder. The granulate was dried, comminuted on a sieve of 1.4 mm mesh size, then the remaining quantity of starch, talc and magnesium stearate was added, carefully mixed and processed into tablets.

EXAMPLE 23

Capsules, each dosed at 0.200 g and containing 20 mg of the active substance can be prepared as follows:

| Composition for 500 capsules | |
|---|---|
| 3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido] propionamidine hydrochloride | 10 g |
| Lactose | 80 g |
| Corn starch | 5 g |
| Magnesium stearate | 5 g |

This formulation can be encapsulated in two-piece hard gelatin capsules and dosed at 0.200 g for each capsule.

EXAMPLE 24

Intramuscular Injection 25 mg/ml

An injectable pharmaceutical composition can be manufactured by dissolving 25 g of 3-[1-methyl-4-[1-methyl-4-[1-ethyl-4-[4-N-methyl-N-(2-chloroethyl)aminobenzene-1-carboxamido]pyrrole-2-carboxamido]pyrrole-2-carboxamido]pyrrole-2-carboxamido]propionamidine hydrochloride in sterile propyleneglycol (1000 ml) and sealing ampoules of 1,5 ml.

What is claimed is:

1. A distamycin derivative of formula (I):

wherein:

$n$ is 2, 3 or 4;

$R_0$ is $C_1$–$C_4$ alkyl or —$CH_2CH_2$—$X_2$, wherein $X_2$ is a halogen atom; $R_1$ and $R_2$ are selected, each independently, from: hydrogen, $C_1$–$C_4$ alkyl optionally substituted by one or more fluorine atoms, $C_1$–$C_4$ alkoxy, and halogen;

$X_1$ is a halogen atom;

B is selected from:

wherein $R_6$, $R_7$, $R_8$, and $R_9$ are, each independently, hydrogen or $C_1$–$C_4$ alkyl, and m is 0, 1 or 2; with the proviso that when $R_0$ is —$CH_2CH_2$—$X_2$, B is different from —$(CH_2)_m$—$NR_6R_7$;

or a pharmaceutically acceptable salt thereof.

2. A compound according to claim 1, wherein:

n is 3;

$X_1$ is chloro or bromo;

$R_0$ is methyl, ethyl, n-propyl or i-propyl, $R_1$ and $R_2$ are, each independently, hydrogen, —$CH_3$, —$OCH_3$, or —$CF_3$;

B is selected from:

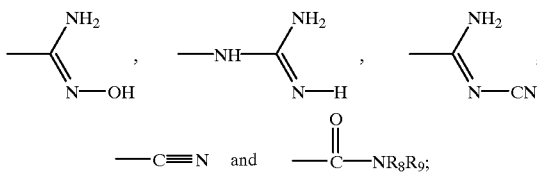

wherein $R_8$ and $R_9$ are, each independently, hydrogen or methyl; or the pharmaceutically acceptable salts thereof.

3. A compound according to claim 1, wherein:
n is 3;
$R_0$ is —$CH_2CH_2$—$X_2$;
$X_1$ and $X_2$ are chloro or bromo;
$R_1$ and $R_2$ are each independently, hydrogen, —$CH_3$, or —$OCH_3$;
B is selected from:

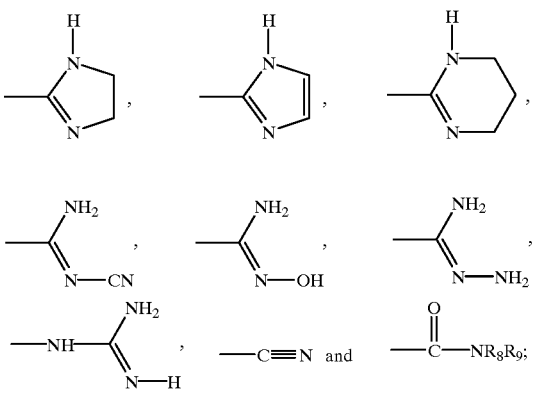

wherein $R_8$ and $R_9$ are, each independently, hydrogen or methyl;
or the pharmaceutically acceptable salts thereof.

4. A compound according to claim 1, selected from:
3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propionamidoxime;
3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propionamidoxime;
3-[1-methyl-4-1-methyl-4-[1-methyl-4-[3-methyl-4-N-ethyl-N-(2-chloroethyl)aminobenzene-1-carboxamido]pyrrole-2-carboxamido]pyrrole-2-carboxamido]propionamidoxime;
3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propionamidoxime;
3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propionamidoxime;
3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propionamidoxime;
3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propionamidoxime;
3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propionamidoxime;
3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propioncyanamidine;
3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propioncyanamidine;
3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propioncyanamidine;
3-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]propioncyanamidine;
3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propioncyanamidine;
3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propioncyanamidine;
3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propioncyanamidine;
3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propioncyanamidine;
2-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]ethylguanidine;
2-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]ethylguanidine;
2-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]ethylguanidine;
2-[1-methyl-4-[1-methyl-4-[1-methyl-4-[3,5-dimetyl-4-N-ethyl-N-(2-chloroethyl)aminobenzene-1-carboxamido]pyrrole-2-carboxamido]pyrrole-2-carboxamido]pyrrole-2-carboxamido]ethylguanidine;
2-[1-methyl-4-[1-methyl-4-[1-methyl-4-[3-methoxy-4-N-ethyl-N-(2-chloroethyl)aminobenzene-1- carboxamido]pyrrole-2-carboxamido]pyrrole-2-carboxamido]pyrrole-2-carboxamido]ethylguanidine;

2-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]ethylguanidine;

2-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]ethylguanidine;

2-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]ethylguanidine;

2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-(2-imidazoline);

2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazoline);

2-[1-methyl-4-[1-methyl-4-[1-methyl-4-[4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)];

2-[1-methyl-4-[1-methyl-4-[1-methyl-4-[3-methyl-4-N,N-bis(2-chloroethyl)aminobenzene-1-carboxamido]pyrrole-2-carboxamido]pyrrole-2-carboxamido]pyrrole-2-carboxamido]ethyl-1-[2-(3,4,5,6-tetrahydropirimidine)];

2-[1-methyl-4[1-methyl-4-[1-methyl-4[4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3,5-dimethyl-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

2-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]ethyl-1-(2-imidazole);

3-[1-methyl-4[1-methyl-4[1-methyl-4[4-N,N-bis(2-chloroethyl)aminobenzene-1-carboxamido]pyrrole-2-carboxamido]pyrrole-2-carboxamido]pyrrole-2-carboxamido]propionamidoxime;

3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionamidoxime;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[3,5-dimethyl-4-N,N-bis(2-chloroethyl)aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[3-methoxy-4-N,N-bis(2-chloroethyl)aminobenzene-1-carboxamido]pyrrole-2-carboxamido]pyrrole-2-carboxamido]pyrrole-2-carboxamido]propioncyanamidine;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionamidrazone;

3-[1-methyl-4[1-methyl-4[1-methyl-4[3-methyl-4-N,N-bis(2-chloroethyl)aminobenzene-1-carboxamido]pyrrole-2 -carboxamido]pyrrole-2-carboxamido]pyrrole-2-carboxamido]propionamidrazone;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionitrile;

3-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]propionitrile;

2-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]ethylguanidine;

2-[1-methyl-4[1-methyl-4[1-methyl-4[3-methyl-4-N,N-bis(2-chloroethyl)aminobenzene-1-carboxamido]pyrrole-2-carboxamido]pyrrole-2-carboxamido]pyrrole-2-carboxamido]ethylguanidine;

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[4-N-propyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-methyl-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3,5-dimethyl-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-methoxy-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-trifluoromethyl-4-N-ethyl-N-(2-chloroethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[4-N-ethyl-N-(2-bromoethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[3-methyl-4-N-ethyl-N-(2-bromoethyl)aminobenzene-1-carboxamido]pyrrole-2-carboxamido]pyrrole-2-carboxamido]pyrrole-2-carboxamido]propionamide;

3-[1-methyl-4-[1-methyl-4-[1-methyl-4-[4-N-ethyl-N-(2-chloroethyl)aminobenzene-1-carboxamido]pyrrole-2-carboxamido]pyrrole-2-carboxamido]pyrrole-2-carboxamido]propion-N-methyl-amide;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propionamide;

3-[1-methyl-4[1-methyl-4[1-methyl-4[3-methyl-4-N,N-bis(2-chloroethyl)aminobenzene-1-carboxamido]pyrrole-2 -carboxamido]pyrrole-2-carboxamido]pyrrole-2-carboxamido]propionamide;

3-[1-methyl-4[1-methyl-4[1-methyl-4[4-N,N-bis(2-chloroethyl) aminobenzene-1-carboxamido]pyrrole-2-carboxamido]pyrrole-2-carboxamido]pyrrole-2-carboxamido]propion-N-methyl-amide;

3-[1-methyl-4[1-methyl-4[1-methyl-4[4-N,N-bis(2-bromoethyl) aminobenzene-1-carboxamido]pyrrole-2-carboxamido]pyrrole-2-carboxamido]pyrrole-2-carboxamido]propionamidoxime;

3-[1-methyl-4[1-methyl-4[1-methyl-4[4-N,N-bis(2-bromoethyl) aminobenzene-1-carboxamido]pyrrole-2-carboxamido]pyrrole-2-carboxamido]pyrrole-2-carboxamido]propionitrile;

or the pharmaceutically acceptable salts thereof.

5. A process for preparing a compound according to claim 1, which comprises;

(A) (a) reacting a compound of formula (II):

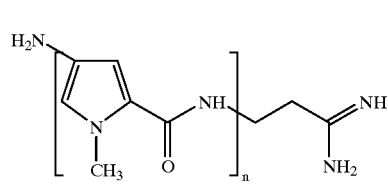

(II)

wherein n is 2, 3 or 4, with a compound of formula (III):

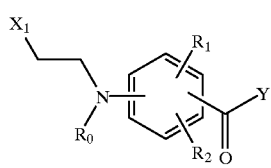

(III)

wherein:

$R_0$ is $C_1$–$C_4$alkyl or —$CH_2CH_2$—$X_2$, wherein $X_2$ is a halogen atom;

$R_1$ and $R_2$ are selected, each independently, from: hydrogen, $C_1$–$C_4$ alkyl optionally substituted by one or more fluorine atoms, $C_1$–$C_4$ alkoxy, and halogen;

$X_1$ is a halogen atom; and

Y is hydroxy or a leaving group;

to obtain a compound of formula (IV):

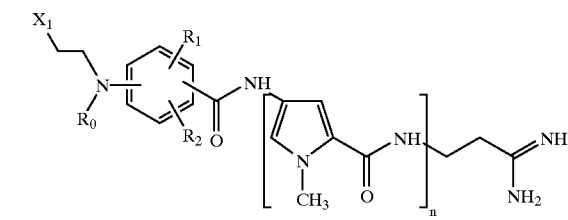

(IV)

and reacting the compound of formula (IV) with:

(i) $H_2N$—$(CH_2)_p$—$NH_2$, where p is 2 or 3, to obtain a compound of formula (I) wherein B is:

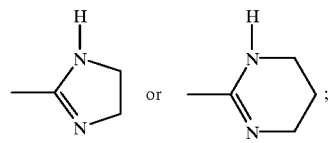

(ii) $H_2N$—$CH_2$—CHO to obtain a compound of formula (I) wherein B is:

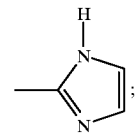

(iii) $H_2N$—CN to obtain a compound of formula (I) wherein B is:

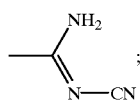

(iv) $H_2N$—OH to obtain a compound of formula (I) wherein B is:

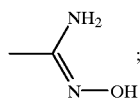

(v) $H_2N$—$NH_2$ to obtain a compound of formula (I) wherein B is:

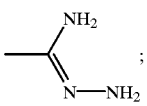

(vi) succinic anhydride to obtain a compound of formula (I) wherein B is —C≡N;

(vii) water in an alkaline medium, to obtain a compound of formula (I) wherein B is —CO—$NR_8R_9$ with $R_8$ and $R_9$ equal to hydrogen; or (viii) $HNR_8R_9$ to obtain a compound of formula (I) wherein B is:

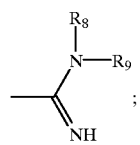

and reacting the compound of formula (I) thus obtained with water in an alkaline medium, to obtain a compound of formula (I) wherein B is —CO—NR$_8$R$_9$, with R$_8$ and R$_9$, each independently, equal to hydrogen or C$_1$–C$_4$ alkyl, with the proviso that at least one of R$_8$ and R$_9$ is C$_1$–C$_4$ alkyl;

or:

(b) reacting a compound of formula (V):

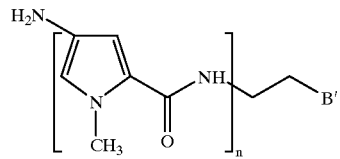
(V)

wherein n is 2, 3 or 4; B' is selected from:

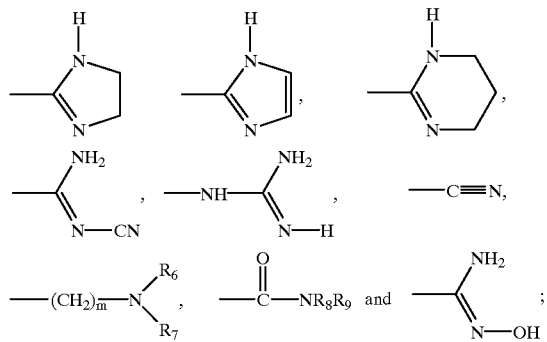

wherein R$_6$, R$_7$, R$_8$ and R$_9$ are each independently hydrogen or C$_1$–C$_4$ alkyl, and m is 0, 1 or 2;

with a compound of formula (III):

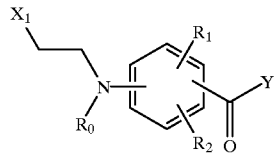
(III)

wherein:
R$_0$ is C$_1$–C$_4$ alkyl or —CH$_2$CH$_2$—X$_2$, wherein X$_2$ is a halogen atom;
R$_1$ and R$_2$ are selected, each independently, from: hydrogen, C$_1$–C$_4$ alkyl optionally substituted by one or more fluorine atoms, C$_1$–C$_4$ alkoxy, and halogen;
X$_1$ is a halogen atom; and
Y is hydroxy or a leaving group;
to obtain a compound of formula (I) wherein B is B' as defined above, with the proviso that when R$_0$ is —CH$_2$CH$_2$—X$_2$, B and B' are different from —(CH$_2$)$_m$—NR$_6$R$_7$; and (B) if necessary converting the thus obtained compound of formula (I) into a pharmaceutically acceptable salt thereof.

6. A method of making a medicament for treating a viral infection or cancer, comprising mixing a compound of claim 1 with a pharmaceutically acceptable carrier.

7. A method of treating a viral infection in a mammal in need of the treatment, comprising administering a viral infection treating effective amount of a compound of claim 1 to said mammal.

8. The method of claim 7, wherein said mammal is a human.

9. A method of treating a viral infection in a mammal in need of the treatment, comprising administering a viral infection treating effective amount of a compound of claim 4 to said mammal.

10. The method of claim 9, wherein said mammal is a human.

11. A method of treating cancer in a mammal in need of the treatment, comprising administering a cancer treating effective amount of a compound of claim 1 to said mammal.

12. The method of claim 11, wherein said mammal is a human.

13. A method of treating cancer in a mammal in need of the treatment, comprising administering a cancer treating effective amount of a compound of claim 4 to said mammal.

14. The method of claim 13, wherein said mammal is a human.

15. A pharmaceutical composition, which comprises a compound according to any one of claims 1 to 4 as an active principle, in association with a pharmaceutically acceptable carrier.

* * * * *